US012569622B2

(12) United States Patent
McCullough et al.

(10) Patent No.: US 12,569,622 B2
(45) Date of Patent: Mar. 10, 2026

(54) SYSTEMS AND METHODS FOR REMOTELY PROCESSING DATA COLLECTED BY A DRUG DELIVERY DEVICE

(71) Applicant: AMGEN INC., Thousand Oaks, CA (US)

(72) Inventors: Adam B. McCullough, Westlake Village, CA (US); Basel Hasan Taha, Westlake Village, CA (US); Jimmie L. Ward, Camarillo, CA (US); Christopher R. Folk, San Diego, CA (US); Steven William Badelt, Los Angeles, CA (US); Ferry Tamtoro, San Ramon, CA (US); Huaying Yang, Vernon Hills, IL (US); Mark Ka Lai Lee, Newbury Park, CA (US); Desheng Yin, Thousand Oaks, CA (US); Scott R. Gibson, Thousand Oaks, CA (US); Donald Busby, Thousand Oaks, CA (US); Peter V. Shultz, Woodland Hills, CA (US); Keith P. Kogler, Simi Valley, CA (US)

(73) Assignee: AMGEN INC., Thousand Oaks, CA (US)

( * ) Notice: Subject to any disclaimer, the term of this patent is extended or adjusted under 35 U.S.C. 154(b) by 362 days.

(21) Appl. No.: 18/111,064

(22) Filed: Feb. 17, 2023

(65) Prior Publication Data
US 2023/0201461 A1 Jun. 29, 2023

Related U.S. Application Data

(63) Continuation of application No. 15/315,896, filed as application No. PCT/US2015/033935 on Jun. 3, 2015, now abandoned.
(Continued)

(51) Int. Cl.
A61M 5/20 (2006.01)
A61M 5/142 (2006.01)
(Continued)

(52) U.S. Cl.
CPC .......... *A61M 5/20* (2013.01); *A61M 5/14244* (2013.01); *A61M 5/14248* (2013.01);
(Continued)

(58) Field of Classification Search
CPC ................ A61M 5/20; A61M 5/14244; A61M 5/14248; A61M 5/158; A61M 5/24;
(Continued)

(56) References Cited

U.S. PATENT DOCUMENTS 3,485,239 A 12/1969 Vanderbeck
4,810,248 A 3/1989 Masters et al.
(Continued)

FOREIGN PATENT DOCUMENTS

AU 2010221666 B2 2/2015
CA 2941425 A1 9/2015
(Continued)

OTHER PUBLICATIONS

Wu, Molecular Therapy, 2007, pp. 1053-1064.*
(Continued)

*Primary Examiner* — Michael I Ezewoko
(74) *Attorney, Agent, or Firm* — MARSHALL, GERSTEIN & BORUN LLP

(57) ABSTRACT
Systems and methods are disclosed for processing sensor data collected by a drug delivery device with an external computing device. The drug delivery device may include a reservoir and a delivery cannula having a proximal end in fluid communication with the reservoir and a distal end to be received within a patient. The drug delivery device may further include one or more sensors configured to generate
(Continued)

sensor data representative of a condition and/or operational state of the drug delivery device, and a communication module configured to transmit information to the external computing device. The external computing device may process the information received from the drug delivery device according to information stored in a memory of the external computing device to determine the condition or the operational state of the drug delivery device and/or generate instructional or informational prompts to be displayed to a user or patient.

27 Claims, 10 Drawing Sheets

Related U.S. Application Data

(60) Provisional application No. 62/007,007, filed on Jun. 3, 2014.

(51) Int. Cl.

| | |
|---|---|
| *A61M 5/158* | (2006.01) |
| *A61M 5/24* | (2006.01) |
| *A61M 5/315* | (2006.01) |
| *A61M 5/32* | (2006.01) |
| *A61M 5/50* | (2006.01) |
| *G06Q 50/00* | (2012.01) |
| *G06Q 50/22* | (2018.01) |
| *G16H 20/17* | (2018.01) |
| *G16H 40/00* | (2018.01) |
| *G16H 40/63* | (2018.01) |
| *G16H 40/67* | (2018.01) |

(52) U.S. Cl.
CPC .............. *A61M 5/158* (2013.01); *A61M 5/24* (2013.01); *A61M 5/31501* (2013.01); *A61M 5/31568* (2013.01); *A61M 5/3202* (2013.01); *A61M 5/3243* (2013.01); *A61M 5/3257* (2013.01); *A61M 5/326* (2013.01); *A61M 5/5086* (2013.01); *G06Q 50/01* (2013.01); *G06Q 50/22* (2013.01); *G16H 20/17* (2018.01); *G16H 40/00* (2018.01); *G16H 40/63* (2018.01); *G16H 40/67* (2018.01); *A61M 2005/3267* (2013.01); *A61M 2205/3331* (2013.01); *A61M 2205/3368* (2013.01); *A61M 2205/3553* (2013.01); *A61M 2205/3576* (2013.01); *A61M 2205/50* (2013.01); *A61M 2205/502* (2013.01); *A61M 2205/52* (2013.01); *A61M 2205/581* (2013.01); *A61M 2205/6009* (2013.01)

(58) Field of Classification Search
CPC .......... A61M 5/31501; A61M 5/31568; A61M 5/3202; A61M 5/3243; A61M 5/3257; A61M 5/326; A61M 5/5086; A61M 2005/3267; A61M 2205/3331; A61M 2205/3368; A61M 2205/3553; A61M 2205/3576; A61M 2205/50; A61M 2205/502; A61M 2205/52; A61M 2205/581; A61M 2205/6009; G16H 20/17; G16H 40/67; G16H 40/63; G16H 40/00; G06Q 50/01; G06Q 50/22
See application file for complete search history.

(56) References Cited

U.S. PATENT DOCUMENTS

| | | | |
|---|---|---|---|
| 5,658,250 A | 8/1997 | Blomquist et al. | |
| 5,991,655 A | 11/1999 | Gross et al. | |
| 6,171,276 B1 | 1/2001 | Lippe et al. | |
| 6,547,755 B1 | 4/2003 | Lippe et al. | |
| 6,893,415 B2 | 5/2005 | Madsen et al. | |
| 7,004,928 B2 | 2/2006 | Aceti et al. | |
| 7,303,549 B2 | 12/2007 | Flaherty et al. | |
| 8,287,454 B2 | 10/2012 | Wolpert et al. | |
| 8,361,026 B2 * | 1/2013 | Edwards | A61M 15/008 604/137 |
| 8,547,239 B2 | 10/2013 | Peatfield et al. | |
| 8,639,288 B1 | 1/2014 | Friedman | |
| 8,707,392 B2 | 4/2014 | Birtwhistle et al. | |
| 9,089,650 B2 | 7/2015 | Nielsen et al. | |
| 9,138,539 B1 | 9/2015 | Friedman | |
| 9,427,529 B2 | 8/2016 | Cabiri | |
| 10,010,275 B2 | 7/2018 | Gottlieb et al. | |
| 10,010,676 B2 | 7/2018 | Bureau | |
| 10,070,822 B2 | 9/2018 | Terashima et al. | |
| 10,092,693 B2 | 10/2018 | Hanson et al. | |
| 10,283,014 B2 * | 5/2019 | Baker | G09B 19/00 |
| 10,773,032 B2 | 9/2020 | Cirillo et al. | |
| 12,251,201 B2 * | 3/2025 | Poltorak | A61B 5/0022 |
| 2001/0049608 A1 | 12/2001 | Hochman | |
| 2002/0040208 A1 | 4/2002 | Flaherty et al. | |
| 2002/0072733 A1 | 6/2002 | Flaherty | |
| 2002/0096543 A1 | 7/2002 | Juselius | |
| 2002/0133113 A1 | 9/2002 | Madsen et al. | |
| 2002/0188419 A1 | 12/2002 | Slate et al. | |
| 2004/0015131 A1 | 1/2004 | Flaherty et al. | |
| 2005/0022274 A1 | 1/2005 | Campbell et al. | |
| 2005/0075670 A1 | 4/2005 | Bengtsson | |
| 2005/0182358 A1 | 8/2005 | Veit et al. | |
| 2005/0227676 A1 | 10/2005 | De Vries | |
| 2005/0277912 A1 | 12/2005 | John | |
| 2006/0178573 A1 | 8/2006 | Kermani et al. | |
| 2006/0263839 A1 | 11/2006 | Ward et al. | |
| 2006/0264835 A1 | 11/2006 | Nielsen et al. | |
| 2007/0060870 A1 | 3/2007 | Tolle et al. | |
| 2007/0106218 A1 | 5/2007 | Yodfat et al. | |
| 2007/0118405 A1 | 5/2007 | Campbell et al. | |
| 2007/0179448 A1 | 8/2007 | Lim et al. | |
| 2008/0014550 A1 | 1/2008 | Jones et al. | |
| 2008/0119705 A1 | 5/2008 | Patel et al. | |
| 2008/0125724 A1 | 5/2008 | Monroe | |
| 2008/0160492 A1 | 7/2008 | Campbell et al. | |
| 2008/0234630 A1 | 9/2008 | Iddan et al. | |
| 2008/0269689 A1 | 10/2008 | Edwards et al. | |
| 2009/0093788 A1 | 4/2009 | Sanchez, Jr. et al. | |
| 2009/0128330 A1 | 5/2009 | Monroe | |
| 2009/0192443 A1 | 7/2009 | Collins, Jr. | |
| 2009/0259194 A1 | 10/2009 | Pinedjian et al. | |
| 2010/0016796 A1 | 1/2010 | Derichs | |
| 2010/0049126 A1 | 2/2010 | Bronfeld et al. | |
| 2010/0160894 A1 | 6/2010 | Julian et al. | |
| 2010/0185142 A1 | 7/2010 | Kamen et al. | |
| 2010/0211005 A1 | 8/2010 | Edwards et al. | |
| 2010/0262117 A1 | 10/2010 | Magni et al. | |
| 2010/0268190 A1 | 10/2010 | Mielenz | |
| 2010/0318035 A1 | 12/2010 | Edwards et al. | |
| 2011/0004188 A1 | 1/2011 | Shekalim | |
| 2011/0081888 A1 | 4/2011 | Waniss | |
| 2011/0111794 A1 | 5/2011 | Bochenko et al. | |
| 2011/0166426 A1 | 7/2011 | Haueter et al. | |
| 2011/0178462 A1 | 7/2011 | Moberg et al. | |
| 2011/0184342 A1 | 7/2011 | Pesach et al. | |
| 2011/0184752 A1 | 7/2011 | Ray et al. | |
| 2011/0213306 A1 | 9/2011 | Hanson et al. | |
| 2011/0270188 A1 | 11/2011 | Caffey et al. | |
| 2011/0270214 A1 | 11/2011 | Jørgensen et al. | |
| 2011/0275410 A1 | 11/2011 | Caffey et al. | |
| 2011/0295215 A1 | 12/2011 | Nielsen et al. | |
| 2011/0313350 A1 | 12/2011 | Krulevitch et al. | |
| 2011/0313395 A1 | 12/2011 | Krulevitch et al. | |
| 2012/0010594 A1 | 1/2012 | Holt et al. | |

(56) References Cited

U.S. PATENT DOCUMENTS

| | | |
|---|---|---|
| 2012/0066140 A1 | 3/2012 | Hegeman et al. |
| 2012/0078181 A1 | 3/2012 | Smith et al. |
| 2012/0132201 A1 | 5/2012 | Pommereau |
| 2012/0197197 A1 | 8/2012 | Iddan et al. |
| 2012/0232520 A1 | 9/2012 | Sloan et al. |
| 2012/0238851 A1 | 9/2012 | Kamen et al. |
| 2013/0079708 A1 | 3/2013 | Wimpenny et al. |
| 2013/0138452 A1 | 5/2013 | Cork et al. |
| 2013/0158501 A1 | 6/2013 | Arnitz |
| 2013/0184640 A1 | 7/2013 | Li |
| 2013/0184649 A1 | 7/2013 | Edwards et al. |
| 2013/0204227 A1 | 8/2013 | Bochenko et al. |
| 2013/0226608 A1 | 8/2013 | Di Lascia et al. |
| 2013/0236872 A1 | 9/2013 | Laurusonis et al. |
| 2013/0261561 A1 | 10/2013 | Deberadine |
| 2013/0296823 A1 | 11/2013 | Melker et al. |
| 2013/0310756 A1 | 11/2013 | Whalley et al. |
| 2013/0317753 A1 | 11/2013 | Kamen et al. |
| 2013/0338480 A1 | 12/2013 | Hann |
| 2013/0345670 A1 | 12/2013 | Rajagopalan et al. |
| 2014/0005596 A1 | 1/2014 | Schuster |
| 2014/0012118 A1 | 1/2014 | Mensinger et al. |
| 2014/0012229 A1 | 1/2014 | Bokelman et al. |
| 2014/0074062 A1 | 3/2014 | Caffey et al. |
| 2014/0088554 A1 | 3/2014 | Li et al. |
| 2014/0107580 A1 | 4/2014 | Momose |
| 2014/0108031 A1 | 4/2014 | Ferrara |
| 2014/0128843 A1 | 5/2014 | Baker et al. |
| 2014/0207099 A1 | 7/2014 | Nagar et al. |
| 2014/0243749 A1 | 8/2014 | Edwards et al. |
| 2014/0322682 A1 | 10/2014 | Baym et al. |
| 2016/0030683 A1 | 2/2016 | Taylor et al. |
| 2017/0098058 A1 | 4/2017 | McCullough et al. |
| 2017/0103186 A1 | 4/2017 | McCullough et al. |
| 2017/0119969 A1 | 5/2017 | McCullough et al. |
| 2017/0124284 A1 | 5/2017 | McCullough et al. |
| 2017/0124285 A1 | 5/2017 | McCullough et al. |

FOREIGN PATENT DOCUMENTS

| | | |
|---|---|---|
| CN | 1697628 A | 11/2005 |
| CN | 101254322 A | 9/2008 |
| CN | 102046227 A | 5/2011 |
| CN | 102413855 A | 4/2012 |
| CN | 102905742 A | 1/2013 |
| CN | 103108665 A | 5/2013 |
| CN | 103285448 A | 9/2013 |
| CN | 103491996 A | 1/2014 |
| CN | 103648552 A | 3/2014 |
| CN | 103702697 A | 4/2014 |
| EP | 1640029 A1 | 3/2006 |
| EP | 2537546 A1 | 12/2012 |
| EP | 2567662 A1 | 3/2013 |
| JP | 2000042103 A | 2/2000 |
| JP | 2004524869 A | 8/2004 |
| JP | 2006-524069 A | 10/2006 |
| JP | 2008516711 | 5/2008 |
| JP | 2008538708 A | 11/2008 |
| JP | 2010535569 A | 11/2010 |
| JP | 2010538797 A | 12/2010 |
| JP | 2011-500154 A | 1/2011 |
| JP | 2011147784 A | 8/2011 |
| JP | 2012508081 A | 4/2012 |
| JP | 2012232179 A | 11/2012 |
| JP | 2013511780 A | 4/2013 |
| JP | 2013512732 A | 4/2013 |
| JP | 2013528107 A | 7/2013 |
| JP | 2014-507963 A | 4/2014 |
| JP | 2014524297 A | 9/2014 |
| JP | 2015513352 A | 5/2015 |
| JP | 2016-512144 A | 4/2016 |
| KR | 20100125972 A | 12/2010 |
| TW | 200803942 A | 1/2008 |
| WO | WO-99/07425 A1 | 2/1999 |
| WO | WO-02/056822 A1 | 7/2002 |

| | | |
|---|---|---|
| WO | WO-2003026726 A1 | 4/2003 |
| WO | WO-2003059422 A1 | 7/2003 |
| WO | WO-2004/004809 A1 | 1/2004 |
| WO | WO-2005077441 A2 | 8/2005 |
| WO | WO-2006/045525 | 5/2006 |
| WO | WO-2006067217 A2 | 6/2006 |
| WO | WO-2006108304 A1 | 10/2006 |
| WO | WO-2006/134153 A1 | 12/2006 |
| WO | WO-2007/075677 A2 | 7/2007 |
| WO | WO-2007/088444 A1 | 8/2007 |
| WO | WO-2007/126851 A2 | 11/2007 |
| WO | WO-2007133389 A2 | 11/2007 |
| WO | WO-2008008281 A2 | 1/2008 |
| WO | WO-2008/114218 A2 | 9/2008 |
| WO | WO-2008117226 A1 | 10/2008 |
| WO | WO-2009/019648 A1 | 2/2009 |
| WO | WO-2009/039203 A2 | 3/2009 |
| WO | WO-2009/098648 A2 | 8/2009 |
| WO | WO-2009/125582 A1 | 10/2009 |
| WO | WO-2009/143255 A1 | 11/2009 |
| WO | WO-2010029054 A1 | 3/2010 |
| WO | WO-2010/037828 A1 | 4/2010 |
| WO | WO-2010/052849 A1 | 5/2010 |
| WO | WO-2010/101740 A1 | 9/2010 |
| WO | WO-2010/135184 A1 | 11/2010 |
| WO | WO-2011/005634 A1 | 1/2011 |
| WO | WO-2011056888 A2 | 5/2011 |
| WO | WO-2011063294 A2 | 5/2011 |
| WO | WO-2011068647 A2 | 6/2011 |
| WO | WO-2011071534 A1 | 6/2011 |
| WO | WO-2011090955 A1 | 7/2011 |
| WO | WO-2011/097487 A2 | 8/2011 |
| WO | WO-2011133823 A1 | 10/2011 |
| WO | WO-2012/073032 A1 | 6/2012 |
| WO | WO-2012/127046 A2 | 9/2012 |
| WO | WO-2012126915 A1 | 9/2012 |
| WO | WO-2012145685 A1 | 10/2012 |
| WO | WO-2012/152628 A1 | 11/2012 |
| WO | WO-2012/160163 A1 | 11/2012 |
| WO | WO-2012153295 A2 | 11/2012 |
| WO | WO-2013016376 A2 | 1/2013 |
| WO | WO-2013024160 A2 | 2/2013 |
| WO | WO-2013033421 A2 | 3/2013 |
| WO | WO-2013033467 A2 | 3/2013 |
| WO | WO-2013/050535 A2 | 4/2013 |
| WO | WO-2013/065055 A1 | 5/2013 |
| WO | WO-2013/160152 A1 | 10/2013 |
| WO | WO-2013/176770 A2 | 11/2013 |
| WO | WO-2013/177135 A1 | 11/2013 |
| WO | WO-2014/005953 A1 | 1/2014 |
| WO | WO-2014/011740 A1 | 1/2014 |
| WO | WO-2014/026937 A1 | 2/2014 |
| WO | WO-2014/037331 A1 | 3/2014 |
| WO | WO-2014/060216 A1 | 4/2014 |
| WO | WO-2014057286 A1 | 4/2014 |
| WO | WO-2014/064691 A2 | 5/2014 |
| WO | WO-2014/066256 A1 | 5/2014 |
| WO | WO-2015048803 A2 | 4/2015 |

OTHER PUBLICATIONS

Korean Patent Application No. 10-2022-7035873, Office Action, dated Jan. 18, 2024.

ONdrugDelivery, Prefilled syringes: The rise of the delivery device portfolio, Frederick Furness Publishing, 2012 edition, Issue No. 36 (Oct. 2012).

OndrugDelivery, Injectable delivery: Wearable bolus injectors, Frederick Furness Publishing Ltd., 2014 edition, Issue No. 51 (Jul. 23, 2014).

European Patent No. 3151882 (Owner Amgen Inc.), Communication of a Notice of Opposition, dated Jan. 14, 2025.

Chinese Patent Application No. 202111156962.2, Office Action, dated Aug. 12, 2024.

Wikipedia, Cloud Computing (Jul. 31, 2008).

U.S. Appl. No. 17/940,422, Final Office Action, dated Jun. 8, 2023.

Office Action, Mexican Patent Application No. MX/A/2016/015853, dated Dec. 8, 2022 and translation thereof.

(56) References Cited

OTHER PUBLICATIONS

"Bar code technology in healthcare", Wikipedia entry, retrieved from the Internet at: <//en.wikipedia.org/w/index.php?title=Barcode_technology_in_healthcare&oldid=580283863> (Nov. 5, 2013).

"Omnipod Insulin Management System—UserGuide", Jan. 2008 (Jan. 1, 2008), XP055209058, Bedford, MA, USA, Retrieved from the Internet: https://www.myomnipod.com/patient_guides/first_gen_user_guide_EN.pdf [retrieved on Aug. 21, 2015].

"The New OmniPod PDM", DiaTribe Learn Making Sense of Diabetes, Jun. 30, 2009.

Australian Patent Application No. 2015271676, Examination Report No. 1, dated Mar. 25, 2019.

Australian Patent Application No. 2015271676, Examination Report No. 2, dated Nov. 15, 2019.

Australian Patent Application No. 2015271676, Examination Report No. 3, dated Mar. 17, 2020.

Australian Patent Application No. 2015271763, Examination Report No. 1, dated May 18, 2019.

Australian Patent Application No. 2015271767, Examination Report No. 1, dated Mar. 16, 2019.

Australian Patent Application No. 2015271767, Examination Report No. 2, dated Nov. 29, 2019.

Australian Patent Application No. 2015271769, Examination Report No. 1, dated Oct. 23, 2019.

Australian Patent Application No. 2020201600, Examination Report No. 1, dated Mar. 9, 2021.

Australian Patent Application No. 2020202096, Examination Report No. 2, dated Feb. 23, 2021.

Australian Patent Application No. 2020204260, Examination Report, dated Nov. 1, 2021.

Australian Patent Application No. 2020204260, Examination Report, dated Nov. 5, 2020.

Australian Patent Application No. 2020257127, Examination Report, dated Oct. 20, 2021.

Australian Patent Application No. 202057127, Examination Report, dated Aug. 23, 2022.

Canadian Patent Application No. 2948005, Examination Report, dated Jul. 30, 2021.

Chinese Patent Application No. 201580028862.8, First Office Action, dated Apr. 12, 2019.

Chinese Patent Application No. 201580029198.9, Decision of Rejection, dated Aug. 8, 2019.

Chinese Patent Application No. 201580029198.9, Official Action (translation) dated Aug. 20, 2018.

Chinese Patent Application No. 201580029198.9, Second Office Action, dated Mar. 1, 2019.

Chinese Patent Application No. 201580029453.X, First Office Action, dated Apr. 16, 2019.

Chinese Patent Application No. 201580029455.9, Office Action, dated Mar. 4, 2019.

Chinese Patent Application No. 201580029455.9, Second Office Action, dated Dec. 18, 2019.

Chinese Patent Application No. 202010550731.9, Office Action, dated Apr. 27, 2022.

Chinese Patent Application No. 202010825780.9, Office Action, dated Dec. 31, 2021.

European Patent Application No. 15728736.8, Communication Pursuant to Rule 164(2) and Article 94(3) EPC, dated Aug. 21, 2019.

European Patent Application No. 15728737.6, Communication Pursuant to Article 94(3) EPC, dated May 17, 2019.

European Patent Application No. 15729033.9, Communication Pursuant to Article 94(3) EPC, dated Jun. 19, 2019.

European Patent Application No. 15729033.9, Communication Pursuant to Article 94(3) EPC, dated Oct. 23, 2020.

European Patent Application No. 15730345.4, Communication pursuant to Article 94(3) EPC, dated Feb. 6, 2019.

European Patent Application No. 15730345.4, Communication Pursuant to Rule 114(2) EPC, dated Mar. 29, 2022.

European Patent Application No. 22158912.0, Extended European Search Report, dated Jul. 1, 2022.

International Application No. PCT/US2015/033935, International Preliminary Report on Patentability and Written Opinion, mailed Dec. 6, 2016.

International Application No. PCT/US2015/033946, International Preliminary Report on Patentability and a Written Opinion, mailed Dec. 6, 2016.

International Application No. PCT/US2015/033946, International Search Report and Written Opinion, mailed Feb. 26, 2016.

International Patent Application No. PCT/US2015/033925, International Preliminary Report on Patentability and a Written Opinion, mailed Dec. 6, 2016.

International Preliminary Report on Patentability and Written Opinion for Application No. PCT/US2015/033933, mailed Dec. 6, 2016.

International Preliminary Report on Patentability and Written Opinion for International Application No. PCT/US2015/033939, mailed Dec. 6, 2016.

International Search Report and a Written Opinion for Application No. PCT/US2015/033933, mailed Nov. 5, 2015.

International Search Report and Written Opinion for Application No. PCT/US2015/033925, mailed Nov. 3, 2015.

International Search Report and Written Opinion for Application No. PCT/US2015/033935, mailed Aug. 12, 2015.

International Search Report and Written Opinion for International Application No. PCT/US2015/033939, mailed Sep. 10, 2015.

Israel Patent Application No. 248731, Office Action, dated Dec. 12, 2019.

Israel Patent Application No. 248756, Office Action, dated Dec. 26, 2019.

Japanese Patent Application No. 2016-570990, Notice of Reasons of Rejection, mailed Apr. 2, 2019.

Japanese Patent Application No. 2016-570991, Notice of Rejection, mailed Apr. 2, 2019.

Japanese Patent Application No. 2016-571023, Notice of Rejection, mailing date Apr. 2, 2019.

Japanese Patent Application No. 2016-571049, Notice of Rejection, May 21, 2019.

Japanese Patent Application No. 2020-203182, Notice of Rejection, mailed Oct. 12, 2021.

Japanese Patent Application No. 2020-213220, Office Action, dated Sep. 28, 2021.

Patil et al., Preliminary design of remotely used and monitored medication dispenser, 2006 International Conference of the IEEE Engineering in Medicine and Biology Society, pp. 3616-3619 (2006).

Singapore Patent Application No. 11201609963P, Examination Report, dated May 30, 2018.

Singapore Patent Application No. 11201609970V, Examination Report, dated May 30, 2018.

Singapore Patent Application No. 11201609970V, Written Opinion, dated Nov. 8, 2017.

Singapore Patent Application No. 11201609972R, Examination Report, dated May 30, 2018.

Singapore Patent Application No. 11201609972R, Written Opinion, dated Nov. 7, 2017.

U.S. Appl. No. 15/315,896, Final Office Action, dated Aug. 23, 2022.

U.S. Appl. No. 15/315,896, Final Office Action, dated Feb. 22, 2021.

U.S. Appl. No. 15/315,896, Nonfinal Office Action, dated Feb. 4, 2022.

U.S. Appl. No. 15/315,896, Nonfinal Office Action, dated Mar. 19, 2020.

U.S. Appl. No. 15/315,896, Nonfinal Office Action, dated Sep. 1, 2020.

U.S. Appl. No. 15/315,922, Final Office Action, dated May 10, 2021.

U.S. Appl. No. 15/315,922, Final Office Action, dated Oct. 1, 2019.

U.S. Appl. No. 15/315,922, Nonfinal Office Action, dated Dec. 31, 2018.

U.S. Appl. No. 15/315,922, Nonfinal Office Action, dated Oct. 21, 2021.

U.S. Appl. No. 15/315,954, Nonfinal Office Action, dated Jun. 14, 2021.

(56) References Cited

OTHER PUBLICATIONS

U.S. Appl. No. 15/315,954, Nonfinal Office Action, dated Mar. 16, 2020.

U.S. Appl. No. 15/315,954, Nonfinal Office Action, dated May 25, 2022.

U.S. Appl. No. 15/931,364, Final Office Action, dated Jun. 7, 2022.

U.S. Appl. No. 15/931,364, Nonfinal Office Action, dated Jan. 18, 2022.

U.S. Appl. No. 15/931,364, Nonfinal Office Action, dated Sep. 9, 2021.

U.S. Appl. No. 16/843,622, Nonfinal Office Action, dated May 5, 2021.

U.S. Appl. No. 15/315,817, Final Office Action, dated Jun. 12, 2019.

U.S. Appl. No. 15/315,817, Nonfinal Office Action, dated Dec. 21, 2018.

U.S. Appl. No. 15/315,823, Final Office Action, dated Sep. 20, 2019.

U.S. Appl. No. 15/315,829, Nonfinal Office Action, dated Oct. 17, 2018.

U.S. Appl. No. 16/843,622, Final Office Action, dated Nov. 18, 2020.

Written Opinion and Search Report for Singaporean Application No. 11201609966S, dated Feb. 1, 2018.

Written Opinion for Singapore Application No. 11201609963P, dated Sep. 26, 2017.

U.S. Appl. No. 17/940,422, Nonfinal Office Action, dated Feb. 10, 2023.

Japanese Patent Application No. 2023/218940, Notice of Reasons for Rejection, dated Feb. 4, 2025.

European Patent Application No. 24163506.9, Extended European Search Report, dated Jul. 8, 2024.

Communication of a Notice of Opposition against European Patent No. 3151882, Amgen Inc. (Proprietor) and Ypsomed AG (Opponent), dated Dec. 23, 2024.

Re-Examination Report (translation), Japanese Patent Application No. 2020-178668, drafting date is Mar. 15, 2024.

Communication of Opposition Against European Patent No. 3152694, Proprietor: Amgen Inc., Opponent: Ypsomed AG, dated Dec. 10, 2024.

U.S. Appl. No. 17/940,422, Nonfinal Office Action, dated Dec. 4, 2024.

Japanese Patent Application No. 2022-129187, Appeal No. 2024-008046, Re-examination Report, dated Jul. 1, 2024.

Korean Patent Application No. 2022-7035873, Office Action, Feb. 5, 2025.

Japanese Patent Application No. 2022-129187, Notice of Rejection, mailed Aug. 15, 2023.

Terahata, "Insulin pumps: Possibility of easier selection due to revision of medical treatment fees," Diabetes Network [online], Soshinsha Co., Ltd., Apr. 16, 2012, retrieved from <https://dm-net.co.jp/calendar/2012/017199.php>.

Japanese Patent Application No. 2023-218940, Decision of Rejection, mailed Jul. 22, 2025.

Custodio et al., A review on architectures and communications technologies for wearable health-monitoring systems, Sensors, 12:13907-46 (2012).

ZigBee Specification, ZigBee Document 053474r20, ZigBee Standards Organization, Sep. 19, 2012.

Chan et al., Smart wearable systems: current status and future challenges, Artificial Intelligence in Medicine, 56:137-56 (2012).

Brief Communication, Opposition Proceedings, European patent No. 3152694, dated Jul. 30, 2025.

Brief Communication, Opposition Proceedings, European patent No. 3152694, dated Aug. 1, 2025.

Summons to attend oral proceedings pursuant to Rule 115(1) EPC, in European Patent No. 3151882, Jul. 24, 2025.

Summons to attend oral proceedings pursuant to Rule 115(1) EPC, European Patent No. 3152694, dated Aug. 11, 2025.

Japanese Patent Application No. 2022-104384, Appeal Notice of Reasons for Rejection, mailed Jun. 10, 2025.

Response submitted by Opponent Ypsomed AG, Opposition Against European Patent No. 3151882, filed Nov. 19, 2025.

Response submitted by Opponent Steinbach, Opposition Against European Patent No. 3151882, filed Dec. 22, 2025.

* cited by examiner

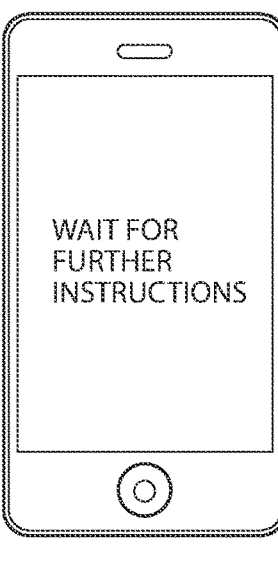
WAIT FOR FURTHER INSTRUCTIONS
*FIG. 7*
AUTOINJECTOR READY FOR USE
*FIG. 8*
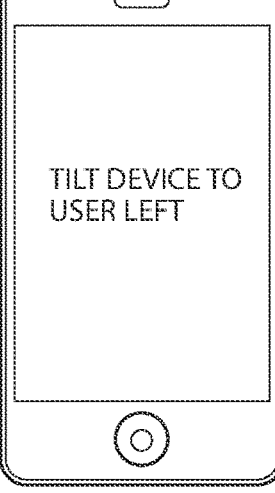
TILT DEVICE TO USER LEFT
*FIG. 9*
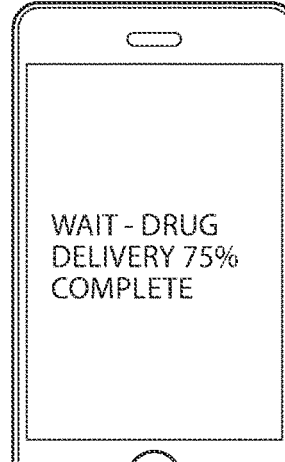
WAIT - DRUG DELIVERY 75% COMPLETE
*FIG. 10*
DELIVERY COMPLETE
PLEASE SAFELY DISCARD DRUG DELIVERY DEVICE
*FIG. 11*

SYSTEMS AND METHODS FOR REMOTELY PROCESSING DATA COLLECTED BY A DRUG DELIVERY DEVICE

CROSS-REFERENCE TO RELATED APPLICATION

This is a continuation of U.S. patent application Ser. No. 15/315,896, filed Dec. 2, 2016, which is the US National Phase of PCT/US15/33935, filed Jun. 3, 2015, which is an application claiming the benefit of priority of U.S. Provisional Patent Application No. 62/007,007, filed Jun. 3, 2014. The entire contents of each of the foregoing are incorporated herein by reference for all purposes.

BACKGROUND

The present disclosure generally concerns systems and methods for use with drug delivery devices and relating to the processing of sensor data collected by the drug delivery devices to determine their condition and/or operational state and improve their usability for patients and other users.

Drugs can be administered through the use of drug delivery devices, such as autoinjectors or on-body injectors or infusers. These devices may replace older delivery systems using the combination of a syringe and a vial containing the drug or medicament, or a pre-filled syringe. Autoinjectors and on-body injectors may be used to automate the injection and delivery or administration process, thereby simplifying the process for certain patient groups or subgroups for which use of the syringe/vial combination or pre-filled syringe systems is disadvantageous, whether because of physiological or psychological impediments.

Even with the use of drug delivery devices, such as autoinjectors, patients may experience challenges during the initial use of the drug delivery device after they have been prescribed a drug that is delivered or administered through the use of a drug delivery device. For example, the user may be uncertain whether the injection should be delayed after a drug delivery device has been removed from cold storage, such as in a refrigerator, and if the injection should be delayed, how long it should be delayed. Additionally, the user may be uncertain whether the medication inside the drug delivery device is the medication prescribed for them. Further, the user may be uncertain whether the medication has expired. Still further, the user may also be uncertain if the actions and their sequence necessary to correctly operate the drug delivery device.

In addition, the condition and use of drug delivery devices is of importance to other parties, such as drug device manufacturers, pharmacies, health care providers and insurers. For instance, information regarding the condition of the drug delivery device along the supply chain may be relevant to whether the drug delivery device will be in good working order when it arrives for use with the patient. Information regarding the location of the drug delivery device along the supply chain may be relevant to the manufacturer and the pharmacy to ensure that adequate supplies are available for the pharmacy to delivery to the user. The compliance information mentioned above may be important to the healthcare providers and insurers, as well as to the patient, because compliance with a therapy regimen may have a direct impact on the success of the therapy.

To address some of the foregoing challenges, it is possible to include one or more sensors onboard the drug delivery device to monitor its condition and use. However, the analysis, storage, communication and other processing of sensor data collected by the one or more sensors may require the use of relatively expensive computer hardware including microprocessors, memories, Internet-accessible communication modules, etc. Since the drug delivery device may be a disposable, single-use device, or otherwise have a limited lifespan, it may be undesirable from an economic perspective to incorporate such expensive computer hardware into the drug delivery device itself.

As set forth in more detail below, the present disclosure sets forth various systems and methods that embody advantageous alternatives to existing drug delivery systems and methods, and that may address one or more of the challenges or needs mentioned above.

SUMMARY

According to an aspect of the disclosure, a system includes a drug delivery device and an external computing device. The drug delivery device may include a reservoir, a delivery cannula having a proximal end in fluid communication with the reservoir and a distal end to be received within a patient, one or more sensors configured to generate sensor data representative of at least one of a condition or an operational state of the drug delivery device, and a first communication module coupled to the one or more sensors and configured to transmit the sensor data. The external computing device may include a second communication module configured to receive the sensor data from the first communication module, a processor coupled to the second communication module, and a memory coupled to the processor. The memory may store non-transitory computer-readable instructions that, when executed by the processor, cause the processor to determine at least one of the condition or the operational state of the drug delivery device based on the sensor data.

According to another aspect of the disclosure, a system includes a drug delivery device and an external computing device. The drug delivery device may include a reservoir, a delivery cannula having a proximal end in fluid communication with the reservoir and a distal end to be received within a patient, one or more sensors, a first communication module, and a first controller coupled to the one or more sensors and the first communication module. The first controller may be configured to use the one or more sensors to determine at least one of a condition or an operational state of the drug delivery device, and control the first communication module to transmit a communication representative of the condition or the operational state of the drug delivery device. The external computing device may include a second communication module configured to receive the communication from the first communication module, a display, a memory, and a second controller coupled to the display, the memory, and the second communication module. The second controller may be configured to control the display to display at least one of an instructional prompt or an informational prompt based on the communication from the first communication module.

According to yet another aspect of the disclosure, a method of using a system comprising a drug delivery device and an external computing device is provided. The drug delivery device may include a reservoir, a delivery cannula having a proximal end in fluid communication with the reservoir and a distal end to be received within a patient, one or more sensors configured to generate sensor data, and a first communication module. The external computing device may include a memory and a second communication module. The method may include: (a) collecting sensor data with the drug delivery device; (b) transmitting the sensor data from the drug delivery device with the first communication module; (c) receiving the sensor data from the drug delivery device at the external computing device with the second communication module; and (d) determining, with the external computing device, at least one of a condition or an operational state of the drug delivery device based on the sensor data.

According to still another aspect of the disclosure, a method of using a system comprising a drug delivery device and an external computing device is provided. The drug delivery device may include a reservoir and a delivery cannula having a proximal end in fluid communication with the reservoir and a distal end to be received within a patient. The external computing device may include a memory. The method may include: (a) determining at least one of a condition or an operational state of the drug delivery device; (b) transmitting a communication representative of the condition or the operational state from the drug delivery device; (c) receiving the communication from the drug delivery device at the external computing device; and (d) processing the communication received from the drug delivery device according to information stored in the memory of the external computing device.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 7 is a simulated screenshot of a display of the local computing device according to a first state subsequent to removal of the drug delivery device from cold storage;

FIG. 8 is a simulated screenshot of a display of the local computing device according to a second state prior to device application;

FIG. 9 is a simulated screenshot of a display of the local computing device according to a third state subsequent to device application but prior to injection;

FIG. 10 is a simulated screenshot of a display of the local computing device according to a fourth state subsequent to injection but prior to completion;

FIG. 11 is a simulated screenshot of a display of the local computing device according to fifth state subsequent to completion;

DETAILED DESCRIPTION

Figure 1:
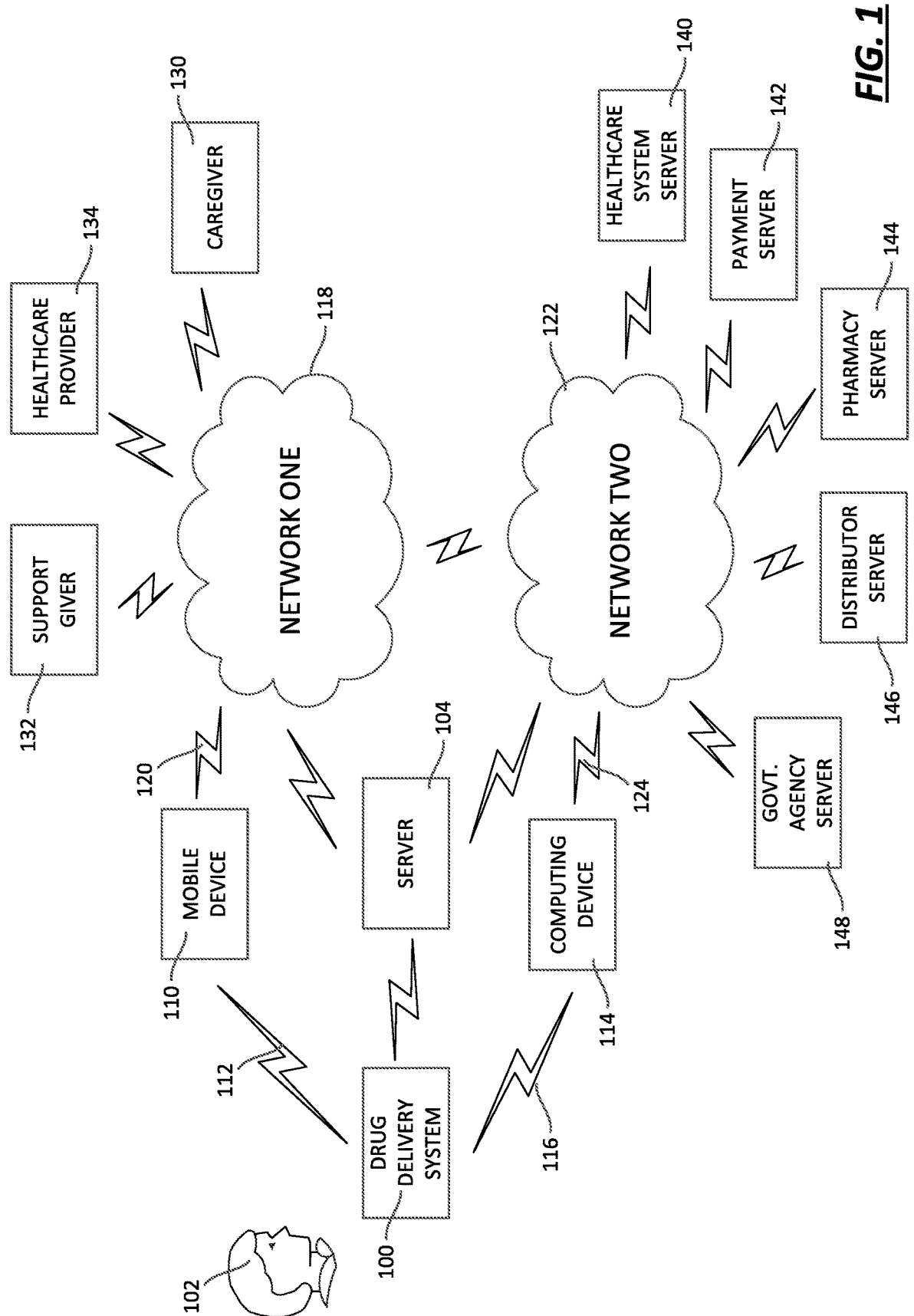
FIG. 1 is a schematic diagram of a drug delivery system according an embodiment of the disclosure in communication with one or more computing devices and one or more networks.

This disclosure is directed to a plurality of systems including a drug delivery device, and to a plurality of methods for using the drug delivery system. In particular, the systems and methods involve the determination of one or more states, which states may be determined through the use of one or more sensors in combination with one or more controllers. The sensors may rely on mechanical, electrical or chemical sensing mechanisms, and the controllers may be mechanical, electrical or electro-mechanical. By way of example and not by way of limitation, the states may relate to the operation of the drug delivery device, or to the condition of the drug delivery device. The system and methods may use the state determination to control the operation of the drug delivery device, and/or may communicate the state determination to other devices, such as third-party servers that may collect, process and/or further disseminate the state determinations received from the system including the drug delivery device, the one or more sensors, and the one or more controllers. In addition or in the alternative, the systems and methods may communicate the state determination to local computing devices, such as a mobile computing device (e.g., cell phone).

A drug delivery system according to the disclosure may include a drug delivery device having a reservoir (which may also be referred to as a primary container, e.g. a syringe, vial or cartridge). The reservoir may contain a drug, which may also be referred to as a medication or a medicament. The drug may be, but is not limited to various biologicals such as peptides, peptibodies, or antibodies. The drug may be in a fluid or liquid form, although the disclosure is not limited to a particular state (e.g., no differentiation is intended between a solution, a gel, or a lyophilized product for example). The drug delivery device also includes delivery cannula having a first end connected to or connectable in fluid communication with the reservoir and a second end to be inserted within a patient. As used herein, the term "delivery cannula" or "cannula" is hereby defined to mean a tube that can be inserted into the body for the delivery of fluid. A cannula may include a rigid or semi-rigid needle or blunt cannula, or may be in a flexible form, by example and not by way of limitation. The cannula may be integrated with the other elements of the drug delivery device, or the cannula may be separate from the other elements of the drug delivery until immediately prior to use. According to certain embodiments, the drug delivery device may further include an inserter to introduce the second end into the patient, although this is not required according to each embodiment of the disclosure. The inserter may or may not be withdrawn back into the device, thereby leaving the cannula in a patient.

Considering the foregoing description of the drug delivery device, the device may be characterized as an autoinjector or an on-body injector or infuser (the reference to injector intended to include also a reference to an infuser, to the extent that a difference is suggested). Autoinjectors may be single-use devices, administering a single dose during a single application of the device to the user's skin, although autoinjectors are not limited to only single-use devices—they may be multi-use devices as well. On-body injectors may be multi-use devices, administering multiple doses during one or more applications of the device to the user's skin, although on-body devices may also be used as single-use devices. Either autoinjectors or on-body injectors may have assemblies or sub-assemblies that are reusable, in that the assemblies may be used and re-used by refilling the reservoir, by removing an empty reservoir and replacing it with a filled reservoir, or by replacing the cannula, for example.

As noted above, the system or method according to the disclosure will determine one or more states relative to the drug delivery device.

For example, the system or method may determine if the drug delivery device is in one or more operational states (i.e., a state relating to the operation of the drug delivery device to deliver the drug to the patient). A non-exhaustive list of the general operational states may include (i) packaged/ready for distribution; (ii) packaged/distributed; (iii) unpackaged/ready for administration; (iv) sterile barrier removed; (v) device applied; (vi) cannula injected (or inserted); (vii) drug delivery initiated; (viii) drug delivery completed; and (ix) device removed. The system or method may determine specific operational states within each of the general operational states; for example, the system or method may determine if plunger has been moved from a first end of a bore (defining a drug reservoir) to a second end of the bore to determine if the drug delivery device is in the "drug delivery complete" state.

Furthermore, the system or method may determine if the drug delivery device is in one or more condition states (i.e., a state relating to the condition of the drug delivery device, not necessarily related to the operation of the drug delivery device to deliver the drug to the patient). A non-exhaustive list of condition states may include (i) age (e.g., taken with respect to a manufacturing date or an expiration date); (ii) sterility/contamination; (iii) temperature; (iv) temperature history; and (iv) orientation. The determination of a condition state may be considered as part of the determination of an operational state; for example, the determination of the temperature state may be considered as part of the determination of the "ready for administration" state. Alternatively, the operational and condition states may be determined separately.

These states may be determined through the use of one or more sensors. The sensors may be particular to a condition state to be determined: for example, a thermocouple disposed adjacent to the reservoir may be used to determine the temperature state of the drug delivery device. The sensors may be particular to an operational state to be determined: for example, a switch may be coupled to a needle guard to determine when a needle cap has been removed to determine the "sterile barrier removed" operational state, the switch being open when the needle cap is disposed over the second end of the cannula and the switch being closed when the needle guard is not disposed over the second end of the cannula. Sensors may be used to determine both a condition state and an operational state: for example, the thermocouple may be used to determine the temperature condition state of the device (or more particularly, the drug), and/or the thermocouple may be used to determine the "ready for administration" operational state.

The system or method may use the determined states to control the operation of the drug delivery device. For example, the system may include a controller that is coupled to the sensor and may be coupled to one or more of the assemblies or subassemblies of the drug delivery device described above, or to one or more additional assemblies or subassemblies of the drug delivery device. The controller may be adapted structurally or programmed (if electrical or electro-mechanical) to activate or to inhibit these assemblies or subassemblies in accordance with the determined states. For example, the drug delivery device may include a lockout that limits or completely inhibits the operation of the injector, and the controller may activate the lockout in a reversible fashion if the temperature state of the drug delivery device (and in particular, the drug in the reservoir) is below, or excessively above, a threshold state.

The system or method may communicate the determined state(s) to another device or system, which communication may be performed in conjunction with use of the determined state(s) to control the operation of the drug delivery device. For example the system or method may communicate the determined state(s) with a networked device using a communication link. In this sense, a networked device is intended to include any device that communicates with at least one other device over a communication link, and might include communication with a device such as mobile device (e.g., cell phone or mobile computing device) using a Bluetooth connection or a computing device using a Wi-Fi connection, for example. The networked device may communicate the determined states to other computing devices remote from the drug delivery system over the network that includes the networked device such as a server. According to certain embodiments of the present disclosure, the system communicates directly with the network (i.e., without an intermediate networked device—the system would be a networked device) or directly with a remote computing device such as a server (using, for example, a 3G antenna). The state information communicated over network, may then be used, for example, to determine if a patient is in compliance, or if a class of drug delivery devices is exhibiting a systemic malfunction. The state information may be used in other manners as well.

The systems and methods may also include control of the drug delivery device according to information relating to the identity of the drug, the drug delivery device, or the user, and/or communication of this identity information. Identity information relating to the drug may include a drug name, a drug concentration, dose information, a lot number or serial number, and a date of manufacture and/or expiration. Identity information relating to the drug delivery device may include a device type (e.g., autoinjector, on-body injector), a lot number or serial number, and a date of manufacture. Identity information relating to the user may include a patient name, demographic information, and patient sub-group information. This information may be referred to as "static" information, in contrast to the state information discussed above.

As to the communication of the information, and in particular relative to the identity information discussed immediately above, it will be recognized that not all information may be useful, desired, or even accessible to every different party whether for convenience, patient privacy or data security concerns.

FIG. 1 illustrates a drug delivery system 100 according to an embodiment of the disclosure. The drug delivery system 100 may be associated with a patient 102, who may use the drug delivery system 100 to inject a drug as part of a therapeutic regime. The drug delivery system 100 may communicate with a computing device (e.g. server) 104 via one or more intermediate computing devices and/or one or more networks. In turn, the server 104 may communicate with the drug delivery system 100, the patient 102, and one or more computing devices (with their associated parties) via one or more intermediate computing devices and/or one or more networks. As is also illustrated in FIG. 1, the server 104 may communicate directly with the drug delivery system 100, using a 3G antenna for example.

For example, the drug delivery system 100 is illustrated as communicating with a mobile computing device 110 (e.g., a smartphone) via a first communication link 112, and with a computing device (e.g., a personal computer or dedicated hub) 114 via a second communication link 116. Both links 112, 116 may operate according to a near field communication protocol, such as Bluetooth, for example. The mobile computing device 110 may communicate with a cellular network 118 via a communication link 120, while the other computing device 114 may communicate with a hard-wired network (e.g., local area network or wide area network) 122 via a communication link 124. These networks 118, 122 may also communicate with the server 104.

The networks 118, 122 may facilitate communication between the server 104 and one or more parties associated with the patient 102, such as his or her caregiver 130, support giver 132, and healthcare provider 134, via their mobile computing devices (e.g., smartphones). The server 104 may also be in communication with one or more computing devices (e.g., servers) associated with one or more additional parties associated with the patient 102. For example, a healthcare system server 140, a payment server 142, a pharmacy server 144, a distributor server 146, and a governmental agency server 148 are illustrated in communication with the server 104 via the network 122. It will also be recognized that the networks 118, 122 may be in communication with each other.

Figure 2:
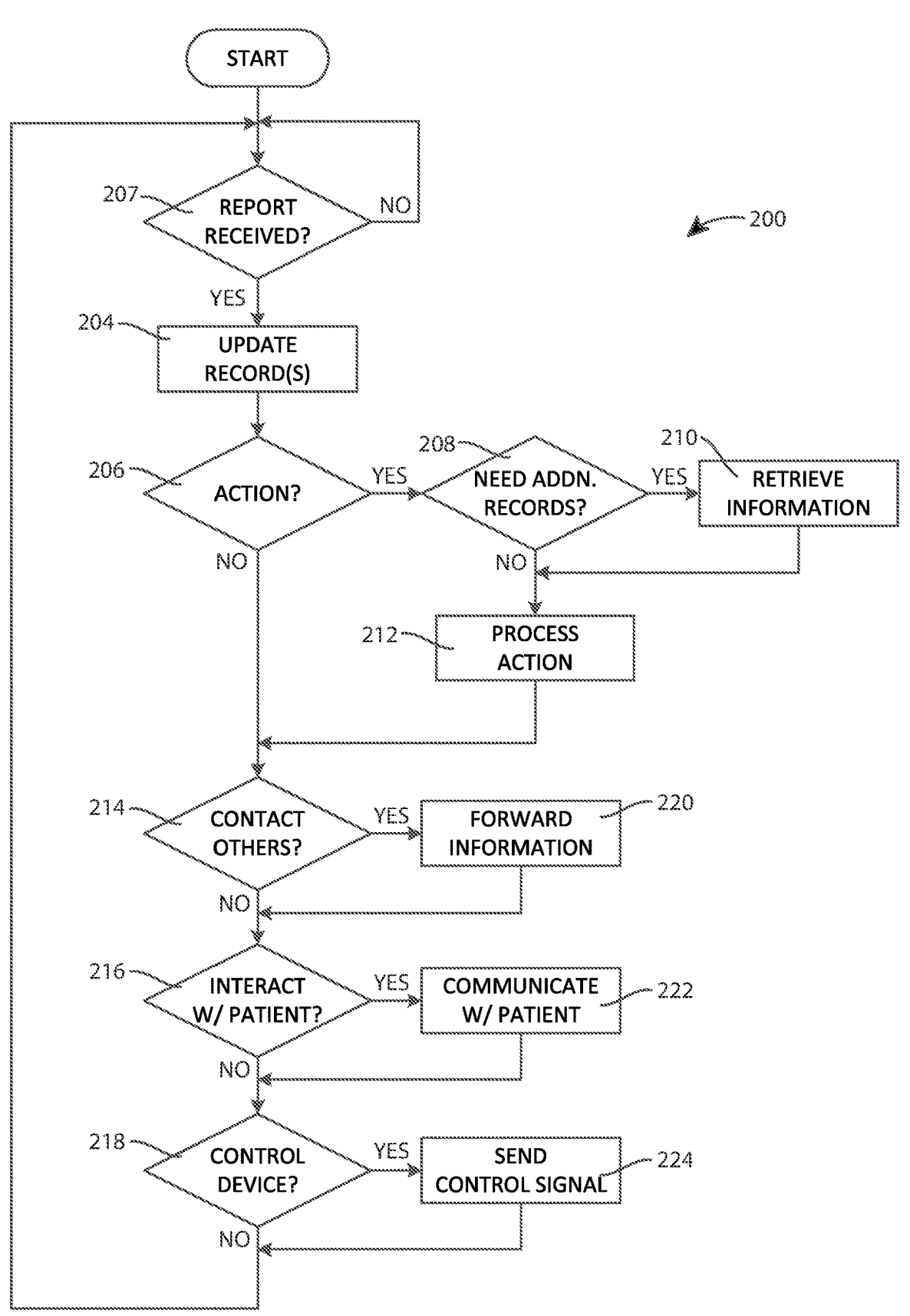
FIG. 2 is a block diagram of a method of operating a drug delivery system according to another embodiment of the disclosure.

Referring to FIG. 2, possible methods of operating one or more computing devices in communication with a drug delivery system are now discussed in the context of a method 200. It will be recognized that the method 200 may be carried out by a single computing device, such as the server 104 illustrated in FIG. 1. Alternatively, the actions discussed with respect to FIG. 2 may be carried out by multiple computing devices, such as the mobile device 110 or computing device 114 in conjunction with the server 104.

The method 200 begins at block 202 with a determination as to whether a report has been received from the drug delivery system. If no report has been received, the method 200 waits at block 202. Once it is determined that a report has been received at block 202, the method 200 proceeds to block 204.

At block 204, the report received from the drug delivery system is used to update one or more records. In this regard, the one or more computing devices adapted or programmed to carry out the method 200 may perform the actions of retrieving the one or more records from storage in one or more memory storage devices, writing the information received from the drug delivery device into the one or more records, and then storing the one or more records in the one or more memory storage devices. The one or more memory storage devices may be part of the one or more computing devices, may be separate from the one or more computing devices, or may include one or more of the memory storage devices that are part of the one or more computing devices and one or more memory storage devices that are separate from the one or more computing devices (i.e., the record is stored at the computing device and in backup storage separate and possibly remote from the computing device).

As mentioned above, the report may be used to update one or more records. For example, there may be one record for the individual patient that is stored in a patient record database. The patient record may be used, for example, to track the compliance of the individual patient (e.g., patient 102) with his or her regime(s). There may also be a record for the drug delivery system used by the individual patient that is stored in a drug delivery system database. The drug delivery system record may be used to store information regarding the drug delivery system throughout the life of the drug delivery system. The drug delivery system record may be accessed by the drug delivery system manufacturer or the drug provider for quality control purposes (e.g., to monitor individual instances of the drug delivery system for faults or failures attributable for to the drug delivery system, or to track the environmental condition histories of one or more drug delivery systems for patterns that may assist in determining improvements in the design, packaging, shipment or handling of the drug delivery systems). There may also be record for drug used in the drug delivery system that is stored in a drug database. This record may be used in a similar fashion to the drug delivery system record for quality control purposes.

In addition to the updating the records at block 204, the computing device adapted or programmed to carry out the method 200 may be adapted or programmed to carry out one or more actions based on the information in the report received from the drug delivery system. For example, the computing device may be adapted or programmed to carry out an action at block 206. This action may require not only the information received in the report and/or stored previously in the record updated at block 204, but may require additional information such as from other patient records, drug system delivery records and/or drug records. If this is the case, the determination may be made at block 208 that these other records need to be accessed, and the information retrieved at block 210 (e.g., by retrieving these other records from the patient, drug delivery system and drug databases and reading the information from these records once retrieved). The action may then be carried out at block 222.

As one example, the one or more computing devices adapted or programmed to carry out the method 200 may be adapted or programmed to use the information received in the report to prepare a compliance history for the patient, which compliance history tracks uses of instances of the drug delivery system by the individual patient relative to his or her treatment regime to determine how successful the patient has been in following the treatment regime and which compliance history may be stored in the patient record. In addition, the one or more computing devices may determine if a pharmacy should be contacted to order delivery of additional drug delivery devices for the individual patient, and may generate a communication to be sent to the pharmacy to order the delivery of additional drug delivery systems. Further, the one or more computing devices may determine if a reminder should be sent to the patient, via the mobile device 110 for example, to improve or support compliance with the individual patient's treatment regime, in which case the one or more computing devices may generate a communication to be sent to the patient or user of the device. Further, the one or more computing devices may determine that the operation of the drug delivery device should be modified because of a conditional state received from the drug delivery device, for example. For example, the one or more computing devices may determine that the drug delivery system should be locked to prevent its use because of the temperature history of the drug in the drug delivery system, for example. In this case, the one or more computing devices may generate a communication, in the form of a signal for example, to be sent to the drug delivery system to lock the drug delivery device that is part of the drug delivery system. Other possible actions are discussed in detail below, although this discussion is for illustrative purposes only and is not intended to be limiting.

Depending on the action taken at block 212, or even if it is determined at block 206 that no action need be taken, the method 200 may proceed to blocks 214, 216, 218 where determinations are made if the computing device should make contact with other parties (block 214), interact with the patient (or user, if not the same as the patient) (block 216) or control the drug delivery device that is part of the drug delivery system (block 218). For example, as discussed above, the action taken at block 212 may involve the generation of communications or signals to be sent to third parties, such as the pharmacy, to the patient, or to the drug delivery device. In such a case, the one or more computing devices may carry out the actions of block 220, 222, 224 as dictated by the determinations made at blocks 214, 216, 218. Alternatively, the one or more computing devices may carry out the actions of blocks 220, 222, 224 even if it is determined that no action need be taken at block 206. For example, the one or more computing devices may forward certain information to third parties 220 based solely on the receipt of the information in a report from the drug delivery device, such that there is no need to separately determine that an action need be taken in regard to the information received (i.e., the communication is automatically sent based on the fact that the information has been received, with the one or more computing devices acting as a repeater station for such information). The receipt of information from the drug delivery device may also prompt communications to be sent to the patient/user or control signals to be sent to the drug delivery system without a separate determination that such action need be taken, the communication or control signal being sent simply because certain information and/or reports were received from the drug delivery system.

Having made the determinations at blocks 214, 216, 218 and carried out the actions of blocks 220, 222, 224, the method 200 may return to block 202 to await the next report. It will be recognized that the one or more computing devices may perform the actions of the method 200 in parallel for each of the reports received from different instances of the drug delivery system, or may perform this steps in sequence for each report. If performed in parallel, the one or more computing devices may determine if action is to be taken in regard to one report, while the one or more computing devices may be interacting with another patient in regard to the information contained in the report received from that patient. Furthermore, the one or more computing devices carrying out the method 200 need not be adapted or programmed to carry out each of the actions described above according to every embodiment of the one or more computing devices. For example, one of the one or more computing devices may be adapted or programmed to update records for each patient and to determine if an interaction with that patient is required, while another of the one or more computing devices may be adapted or programmed to update records for each drug delivery device and to determine is a control signal should be sent to the drug delivery device, while another one of the one or more computing devices does not update any record, but is adapted or programmed to access, for example, a patient record and determine if the pharmacy needs to be contacted to order additional instances of the drug delivery system for the patient associated with the patient record accessed and to generate the communication if the order of additional instances of the system is required.

It will be appreciated that the method 200, above, touches only a fraction of the possible state and identity information that may be used to control and/or monitor the drug delivery device and that may be communicated between the drug delivery system and the one or more computing devices, as well as how that information is used by the drug delivery system and the one or more computing devices. Additional embodiments are possible according to the disclosure.

For example, a non-limiting matrix of state and identity information may include the following:

Condition State Information:
  Temperature
  Shock or vibration exposure
  Light exposure
  Color and/or turbidity (as relates to the drug)
  Orientation
  Geographic position
  Temporal information
Operational State Information:
  Device removed from package
  Device removed from cold storage (e.g., refrigerator)
  Device/drug temperature ready for administration
  Delivery triggered
  Device applied to patient
  Device applied at correct location/orientation on patient
  Cannula inserted into patient and/or inserted into correct tissue
  Delivery in progress
  Delivery complete
  Error has occurred
Device Identity Information:
  Drug name or identification, concentration, and/or amount
  Security and/or anti-counterfeiting information
  Patient prescription/therapeutic regime
Patient Identity Information:
  Point of Care diagnostics on patient
  Self-analyzed measure of progress
  Fingerprint, pin, or other secure identification information This information may be used to control the drug delivery system or device, to be communicated to other computing devices, or otherwise to be used, and an exemplary listing of certain additional uses is included below. The listing and additional comments below is not intended to supersede, but to augment the discussion above, and is intended to be non-limiting.

As one example, the drug delivery system or the one or more computing devices may make a determination regarding the authenticity of the drug and its compliance with manufacturing standards. Such a determination may be made by the drug delivery device at block 208 of method 200, for example. The determination may be made based on the temperature, shock or vibration exposure, and/or light exposure of the drug delivery device/drug (or a history of one or more of these conditions) and color and/or turbidity of the drug (as determined by an optical inspection). This determination may result in control of the drug delivery device to either lock or unlock the device, according to the determination made. See blocks 206-412 and 218, 224 of the method 200.

As another example, the drug delivery system or the one or more computing devices may make a determination whether the drug is appropriate for the patient. See block 206-212 of method 200. The determination may be made based on one or more of the items of device of patient identify information listed above, and may also result in control of the drug delivery device to either lock or unlock the device, according to the determination made. See blocks 206-212 and 218, 224 of method 200.

As a further example, the drug delivery system or the one or more computing devices may make a determination whether the dose has been correctly administered. This determination may be carried out after determining that the drug is appropriate for the patient and/or that the drug is authentic (e.g., not counterfeit) and is in compliance with manufacturing standards. See the preceding paragraphs. The determination whether the dose has been correctly administered may depend on one or more of the types of operational state information listed above. This information may be used to update the patient record, determine the patient compliance or therapy progress, and may prompt communication with the pharmacy regarding a refill, or with the payer (e.g., insurance company) to authorize payment for the drug delivery device. See blocks 204-214 of method 200, and servers 142, 144 of FIG. 1.

As a further alternative, the drug delivery system or the one or more computing devices may use the information to make a determination regarding the operational state of the drug delivery device, and to generate instructional messages to guide the user through the actions required for the proper use of the drug delivery device. The determination may be based on any of the operational state information listed above, and the instructions generated may be dictated by the actions that need to be performed after the operational state that has just occurred. Implementation of interactive instructions that follow the changing states of the drug delivery device may help the user have confidence in administration of the drug.

As a further alternative, the drug delivery system or the one or more computing devices may use the information to make a determination that other people nearby are taking the same medication. See blocks 206-212 of method 200. This determination may be made based on the drug identity information and the patient identity information, in combination with the drug delivery system geographic location information. This determination may prompt a communication with the patient (see blocks 216, 222 of method 200) regarding local support networks of persons with similar conditions and/or taking similar drugs or medication to permit the patient to receive support and encouragement from such networks. Alternatively, the determination may prompt a communication with the local support network(s) (see blocks 214, 220 of method 200) to provide support and encouragement to the patient. As s further alternative, the determination may prompt a personalized intervention communication to be sent to the patient (again, see blocks 216, 222 of method 200).

As a further alternative, the drug delivery system or the one or more computing devices may use the information to make a determination whether the patient is not in compliance with their therapy regime. See blocks 206-212 of method 200. The determination may be based in part on the drug identification information, such as the prescribed treatment regime, in part on condition state information, such as the passage of time, and in part on the operational state information, such as where the drug delivery device is removed from the packaging but where no additional operational state information is determined, reported or received during the passage of time from the removal from packaging operational state. Based on this information, the drug delivery system and/or the one or more computing devices may determine that an interaction with the patient should be generated, such as an alert may be displayed or sent to patient. See blocks 216, 222 of method 200. Furthermore, the drug delivery system and/or one or more computing devices may determine that a communication should be generated to be displayed or sent to a healthcare provider, caregiver, support giver and/or payer to encourage adherence to regime. See blocks 214, 220 of method 200.

As a further alternative, the drug delivery system or the one or more computing devices may use the information to make a determination that the patient needs more medication (a refill). See blocks 206-212 of method 200. The determination may be based in part on the drug identity information, such as the prescribed treatment regime, and in part on the operational state information, such as where the drug delivery has been completed. Based on this information, the one or more computing devices may generate a communication that is sent to the payer and/or pharmacy to request a prescription refill. See blocks 214, 220 of method 200.

As a further alternative, the drug delivery system or the one or more computing devices may use the information to make a determination that the injection was not performed correctly. See blocks 206-212 of method 200. The determination may be based in part on operational state information, in comparison with information that may be collected and stored regarding conventional norms in operation. Alternatively or additionally, a comparison between the determined, reported or received operational states may permit a determination to be made that the injection was not performed correctly. For example, the determination, reporting or receipt of operational state information indicating that the drug delivery is complete without operation state information indicating that device was triggered, that the device was applied to the patient, and/or that the cannula was inserted may indicate that the drug delivery device has failed to perform correctly, is faulty or was operated incorrectly.

As a further alternative, the drug delivery system or the one or more computing devices may use the information to make a determination that patient's condition is improving. The determination may be based in part on patient identity information, such as point-of-care diagnostics performed on the patient (e.g., blood glucose test or other testing) or self-analysis reporting, and in part on the determination, reporting or receipt of operational state information, such as where the drug delivery has been completed. The determination may rely upon an overall trend as opposed to individual determinations or reports, as it is believed that data or reporting trends are usually more indicative of improvement in a patient's condition than the patient's condition as determined at individual instances for serious diseases. As such, the information gathered regarding the patient and the operational state of the drug delivery system/device may be combined with combined with therapy compliance history. This determination may result in individualized interventions to be generated, which interventions (such as encouraging messages and other forms of positive reinforcement) may increase persistence in therapy.

As a further alternative, the drug delivery system or the one or more computing devices may use the information to make a determination of the time of day (or week, month, etc.) that the patient usually takes their medication. This determination may be based, in part, on the patient record in which time information is associated with operational state information, such as relates to the triggering of the drug delivery device or the completion of the drug delivery. This determination may also rely on device identity information, such as the prescribed treatment regime. Based on this determination, the one or more computing devices may generate a reminder communication that is sent, for example, to the mobile device 110 to alert the patient that the time is approaching for them to administer their next dose. As the usefulness of reminders is enhanced when there is reasonable access to the drug delivery device and an opportunity for its use, it is beneficial to reinforce a patients decision to take their medication at a particular time during the day, week, month, etc. Based on this determination, the one or more computing devices may also generate a personalized intervention, such as a message of encouragement to be used as a positive reinforcement.

As a further alternative, the drug delivery system or the one or more computing devices may use the information to make a determination where the patient usually takes their medication. This determination may be based, in part, on the patient record in which geographic position information is associated with operational state information, such as relates to the triggering of the drug delivery device or the completion of the drug delivery. This determination may also rely on device identity information, such as the prescribed treatment regime. Based on this determination, the one or more computing devices may generate a reminder communication that is sent, for example, to the mobile device 110 to alert the patient that the time is approaching for them to administer their next dose when they are at or near the geographic location where the patient usually uses the drug delivery system. As the usefulness of reminders is enhanced when there is reasonable access to the drug delivery device and an opportunity for its use, it is beneficial to reinforce a patient's decision to take their medication when they are in the usual location where they take their medication. Based on this determination, the one or more computing devices may also generate a personalized intervention, such as a message of encouragement to be used as a positive reinforcement.

Of course, the determinations regarding the usual time and location of the use of the drug delivery device may be combined, and the one or more computing devices may generate a message only when the patient or user is at or near their usual location of use at or near the time they usually use the drug delivery device.

While the foregoing has focused principally on the determinations made by the drug delivery system and/or one or more computing devices concerning the patient or the patient's use of the drug delivery device, determinations may be made with reference to the drug delivery device or the drug before the drug delivery device is made available to the patient or user.

For example, the drug delivery system or the one or more computing devices may use the information to make a determination whether delivery of a certain number of doses of a particular drug has arrived (e.g., instances of a drug delivery device containing the particular drug), for example, at a particular distributor or pharmacy location. This determination may be made based in part on the geographic location information and in part on the drug identify information. Based on this information, the one or more computing devices may generate a communication that is sent to the pharmacy or distributor (via the pharmacy or distributor server, for example) to inform them of the delivery of the drug delivery device. The pharmacy or distributor may use such a smart drug delivery device to simplify their logistics and inventory systems, for example.

Along similar lines, the drug delivery system or the one or more computing devices may use the information to make a determination that one or more of the drug delivery devices have been damaged en route to a particular distributor or pharmacy location. The determination may be made based in part on the geographic location information and in part on the drug identify information. The determination may also be based in part on condition state information, such as the temperature, shock/vibration exposure, light exposure or color and/or turbidity of the drug, whether determined at a particular time or over a period of time (i.e., a history as established in the drug delivery device record or the drug record). The determination may also or instead be based in part on the age of the product relative to its manufacture date or expiration date. The determination may also or instead be based in part on operational state information, such as the removal of a sterility barrier from the second end of the cannula of the drug delivery device. Based on this information, the one or more computing devices may generate a communication that is sent to the pharmacy or distributor (via the pharmacy or distributor server, for example) to inform them that the drug delivery device has been damaged or expired. The pharmacy or distributor may use such a smart drug delivery device to expedite the distributor's or the pharmacy's replacement of the damaged or expired product and prevent delays in patient therapy, for example.

As a further alternative, the drug delivery system or the one or more computing devices may use the information to make a determination that the product is as stated and has not been counterfeited. Such a determination may be based on the drug identity information, such as the name, concentration and amount of the product and the security and anti-counterfeiting measures associated with the drug. The determination made by the one or more computing devices may cause a communication to be generated, which communication may be transmitted to a governmental agency (e.g., customs/immigration officials) via the governmental agency server, to distributors and/or pharmacies via their respective servers, and/or patients and caregivers via their personal mobile devices.

As still further alternatives, certain determinations made by drug delivery systems and/or one or more computing devices operating according to embodiments of the disclosure may be used to control the drug delivery device remotely (i.e., without the controlling device being present in the same geographic location (e.g., room, building, or city) as the drug delivery device).

For example, the drug delivery system or the one or more computing devices may use the information to make a determination that the device needs to be controlled to prevent accidental operation. The determination may be based in part on the drug identity information in combination with, for example, certain patient identity information, such as biometric information in the form of a fingerprint. If it is determined that a party that is not authorized to use the drug delivery device is attempting to use the drug delivery device, then the one or more computing devices may generate a signal to be sent to the drug delivery system to lock the drug delivery device or to keep it locked until the drug delivery system is accessed by the patient or user for which it is intended.

As a further alternative, the drug delivery system or the one or more computing devices may use the information to make a determination that the patient associated with the drug delivery device is in a particular group or subgroup of patients or users that require or prefer a particular mode of operation for the drug delivery device. This determination may be made in part using information regarding the identity of the patient and the drug. Based on this determination, the drug delivery system and/or the one or more computing devices may generate a signal that customizes the operation of the drug delivery device. For example, the drug delivery device may be customized as to the sounds and/or lights used to alert the patient to various condition or operational states according to the specific market segment or patient population associated with the patient. As one example, different sounds may be used with pediatric patients than adult patients, louder sounds may be used with patients with hearing loss, and different lights or light sequences may be used with color-blind patients. Such control of the drug delivery device through the drug delivery system and/or one or more computing devices may reduce costs for drug delivery by permitting a single drug delivery device to be used that adapts to patient via software, rather than to use a plurality of different drug delivery device types, each of which has different hardware from the other types of drug delivery devices.

As a further alternative, the drug delivery system or the one or more computing devices may use the information to make a determination that the drug delivery device has not performed properly, and to generate a communication in that regard to the manufacture of the drug delivery device. The manufacturer may then determine modifications and/or improvements to enable proper administration of drug and can implement checks for sensed information and relay errors if it is not followed or is not successful.

As has been mentioned above, the drug delivery system and/or one or more computing devices in communication with the drug delivery system need not be adapted or programmed to carry out every action listed in FIG. 2.

FIGS. 3-14 illustrate additional embodiments of systems and methods in which some or all of the processing of sensor data or other information collected by a drug delivery device is performed by one or more computing devices external to the drug delivery device. Furthermore, the systems and methods of FIGS. 3-14 permit a user to interact with the components of the system to address one or more of the challenges experienced by patients during the initial use of the drug delivery device and/or during the prolonged use of the drug delivery device (e.g., in maintaining adherence with a treatment regimen). To achieve interactivity, the system may sense or determine different types of information regarding the drug delivery device, including operational state information (e.g., whether medicament delivery is complete), condition information (e.g. temperature), and identity information (e.g., the name of the medicament). The drug delivery device may communicate this information to a local and/or remote computing device so that the local and/or remote computing device may provide this information and/or instructions to the user. The communication of the information from the drug delivery device may be based on the type of information to be communicated, for example. The drug delivery device may then determine if the user has taken the correct action in response to the information and/or instructions displayed on the local and/or remote computing device, which information may then be communicated to the local and/or remote computing device for further processing.

In general, to achieve the foregoing functionalities, the systems and methods illustrated in FIGS. 3-14 may have an associated controller (which controller may include a processor and memory) that is in communication with a first communication module (which may be a transmitter, a transmitter and receiver pair, or a transceiver), the first communication module may be connected via a communication link to a second communication module (which may be a receiver, a transmitter and receiver pair, or a transceiver) associated with the local and/or remote computing device (which computing device may also include a controller with a processor and memory). The local computing device may be in communication with the remote computing device, such that the drug delivery device (or more particularly, the controller associated with the drug delivery device) may communicate with the local computing device over a first communication link, and then the local computing device may communicate with the remote computing device over a second communication link.

While the drug delivery device described below is configured as an autoinjector, in other embodiments, the drug delivery device may be configured as a on-body injector.

Figure 3:
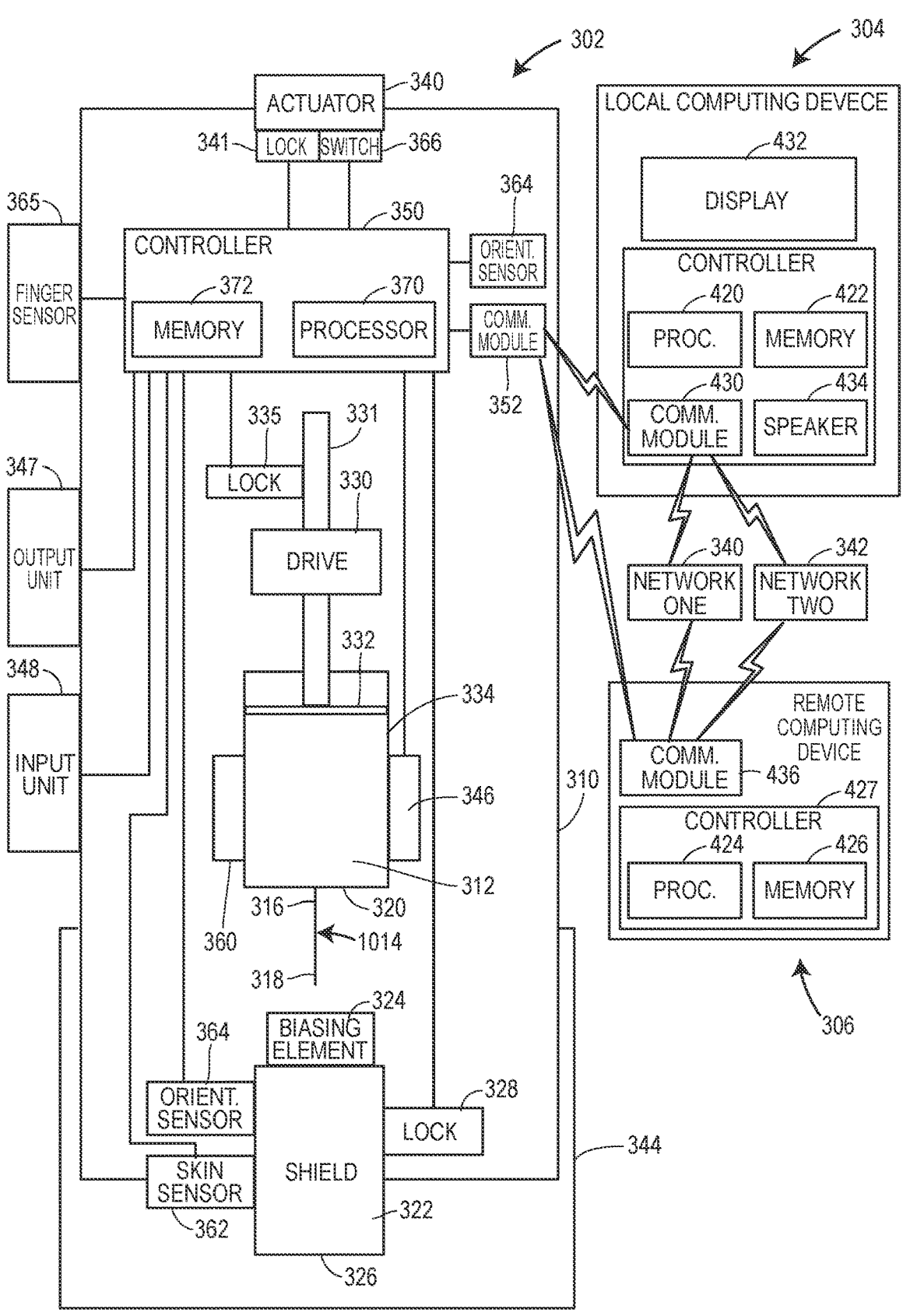
FIG. 3 is a schematic illustration of a system including a drug delivery device, a local computing device, and a remote computing device interconnected with communication links and networks.

FIG. 3 illustrates an embodiment of a system 300 including a drug delivery device 302, a local computing device 304 and a remote computing device 306. While the system 300 includes both a local computing device 304 and a remote computing device 306, not all embodiments according to this disclosure include both a local computing device 304 and a remote computing device 306.

The drug delivery device 302 may be in the form of an autoinjector, and thus is adapted for hand-held use and application against the skin of the patient. The drug delivery device 302 includes a housing 310 in which are disposed assemblies or structures that introduce a delivery cannula into the patient, and that eject a drug or medicament from a reservoir 312 through the delivery cannula into the patient. According to certain embodiments, the same assemblies or structures that introduce the delivery cannula into the patient may also eject the drug or medicament from the reservoir through the delivery cannula into the patient. The drug delivery device 302 may also include assemblies or structures that connect the delivery cannula to the reservoir, that withdraw the delivery cannula into the housing 310 through an opening in the housing 310 (not illustrated), or that deploy other structures that will prevent contact with the delivery cannula once the delivery cannula has been removed from the patient. Even additional assemblies and structures are possible. The specific embodiment of the drug delivery device 302 discussed below is thus by way of example and not by way of limitation.

Accordingly, the drug delivery device 302 includes a reservoir 312 and a delivery cannula 314 having a first end 316 (e.g., a proximal end) that may be connected or connectable in fluid communication with the reservoir 312 and a second end 318 (e.g., a distal end) that may be inserted into a patient. The delivery cannula 314 may be, for example, a rigid needle having a beveled edge that may be sized such that the second end 318 of the needle 314 is received under the skin so as to deliver a subcutaneous injection of the medicament within the reservoir 312. The first end 316 of the needle 314 may be disposed through a wall 320 of the reservoir 312, and thus be connected in fluid communication with the reservoir 312. Alternatively, the first end 316 of the needle 314 may be disposed only partially through the wall 320 (which wall 320 may be a resalable septum or stopper, for example) such that the first end of the needle 314 may not be connected in fluid communication until the second end 318 of the needle 314 is inserted into the patient. In such a circumstance, the first end 316 of the needle 314 may thus be described as connectable in fluid communication with the reservoir 312, although it will be recognized that there are other mechanisms by which the first end 316 of the needle 314 may be connectable, but not connected, in fluid communication with the reservoir 312.

The drug delivery device 302 includes a shield 322 (e.g., a needle shield) that may be deployed at least after the injection has been completed to limit access to the second end 318 of the needle 314. According to certain embodiments, the shield 322 may have a biasing element 324 (such as a spring) that extends the shield 322 from the housing 310 such that a distal end 326 of the shield 322 extends beyond the second end 318 of the needle 314 except when the shield 322 is disposed against the skin and the insertion of the needle 314 is actuated. In fact, the insertion of the needle 314 may be actuated according to certain embodiments of the drug delivery device 302 by disposing the distal end 326 of the shield 322 on or against the skin of the patient.

The drug delivery device 302 may also include a lock 328 (e.g., a ratchet) that is coupled to the shield 322 and configured to limit or prevent movement of the shield 322 relative to the housing 310 of the drug delivery device 302 such that the distal end 326 of the shield 322 extends from the housing 310 a sufficient distance to limit or prevent contact with the second end 318 of the needle 314, for example, after the needle 314 has been removed or separated from the skin of the patient. In some embodiments, the lock 328 may be coupled to a controller (e.g., controller 350 described in more detail below) which can selectively activate or deactivate the lock 328 based on different types of information regarding the drug delivery device 302, including operational state information, condition information, and/or identity information, in accordance with one or more of the methods described above. When the lock 328 is activated by the controller 350, the lock 328 may be configured to limit or prevent movement of the needle shield 322 relative to the housing 310. When the lock 328 is deactivated by the controller 350, the lock 328 may be configured to allow movement of the needle shield 322 relative to the housing 310.

The drug delivery device 302 also includes at least one drive 330 that may be used to insert the second end 318 of the needle 314 into the skin of the patient, and to eject the drug or medicament from the reservoir 312 through the delivery cannula 314 into the patient. The drive 330 may include one or more springs, according to certain embodiments. According to other embodiments, the drive 330 may include a source of pressurized gas or a source of a material that undergoes a phase change, such that the escaping gas or phase changing material provides a motive force that may be applied to the reservoir 312 to eject the drug therefrom. According to still other embodiments, the drive 330 may include an electromechanical system, such as may include a motor for example, although such an electromechanical system may be more appropriate for the on-body autoinjector or infuser described above. Other embodiments of the drive 330 are also possible.

In one embodiment, the drive 330 may be coupled to a plunger 331 and/or a stopper 332 (e.g., a wall) disposed in the reservoir 312 to move that stopper 332 in a distal direction toward the delivery cannula 314. In accordance with such an embodiment, the stopper 332 may be a stopper that is fixed to a distal end of the plunger 331 and received within a bore 334. The plunger 331, in conjunction with the drive 330, may move the stopper 332 along a longitudinal axis of the drug delivery device 302 through the bore 334 from a proximal end of the bore 334 to a distal end of the bore 334, and thereby eject the medicament from the reservoir 312.

In some embodiments, the drive 330 may also cooperate with the stopper 332 and/or the bore 334 to move the reservoir 312 relative to the housing 310 so as to move the second end 318 of the needle 314 relative to the housing 310 and into the patient. According to those embodiments wherein the drive 330 cooperates with the stopper 332, this may occur before the first end 316 of the needle 314 is in fluid communication with the reservoir 312. According to those embodiments wherein the drive cooperates with the bore 334, the drive may include one component (e.g., first spring) that cooperates with the bore 334 to move the reservoir 312 and needle 314 relative to the housing 310, and a second component (e.g., second spring) that cooperates with the stopper 332 to move the stopper 332 relative to the bore 334.

The drug delivery device 302 may also include a lock 335 that is coupled to the plunger 331 and configured to limit or prevent movement of the plunger 331 relative to the housing 310 of the drug delivery device 302 so that the stopper 332 cannot be advanced to discharge the medicament from the reservoir 312 to the patient. In some embodiments, the lock 335 may be coupled to a controller (e.g., controller 350 described in more detail below) which can selectively activate or deactivate the lock 335 based on different types of information regarding the drug delivery device 302, including operational state information, condition information, and/or identity information, in accordance with one or more of the methods described above. When the lock 335 is activated by the controller 350, the lock 335 may be configured to limit or prevent movement of the plunger 331 relative to the housing 310. When the lock 335 is deactivated by the controller 350, the lock 328 may be configured to allow movement of the plunger 331 relative to the housing 310.

The drive 330 may be associated with an actuator 340. The actuator 340 may activate the drive 330 to cause the drive 330 to insert the needle 314 and eject the drug from the reservoir 312 through the needle 314 into the patient. The actuator 340 may, according to certain embodiments, be the needle shield 322, as explained above. According to other embodiments, such as the one illustrated in FIG. 3, the actuator 340 may be a button that may be manually depressed by the user or patient once the drug delivery device 302 is placed disposed on or against the patient's skin. A lock 341 may be coupled to the actuator 340 and configured to limit or prevent movement of the actuator 340 so that the actuator 340 cannot be used to activate the drive 330. In some embodiments, the lock 341 may be coupled to a controller (e.g., controller 350 described in more detail below) which can selectively activate or deactivate the lock 341 based on different types of information regarding the drug delivery device 302, including operational state information, condition information, and/or identity information, in accordance with one or more of the methods described above. When the lock 341 is activated by the controller 350, the lock 341 may be configured to limit or prevent movement of the actuator 340 relative to the housing 310. When the lock 341 is deactivated by the controller 350, the lock 341 may be configured to allow movement of the actuator 340 relative to the housing 310.

The drug delivery device 302 may also include a removable sterile barrier 344 that is disposed about one or more of a distal end of the housing 310, the needle shield 322, and the second end 318 of the delivery cannula 314. The removable sterile barrier 344 may be removably attached to the distal end of the housing 310 as shown in FIG. 3. In some embodiments, the removable sterile barrier 344 may form an interference or snap fit with the distal end of the housing 310. A frictional force associated with the interference or snap fit may be overcome by manually pulling the removable sterile barrier 344 in a direction away from a housing 310. The removable sterile barrier 344, when attached to the drug delivery device 302, may reduce the risk of contamination of the delivery cannula 314 and other elements disposed within the drug delivery device 302.

Additionally, the drug delivery device 302 may include a heating element 346 coupled to the exterior of the reservoir 312 and configured to warm the medicament inside the reservoir 312 through, for example, conductive heating. The heating element 346 may be coupled to the controller 350 so that the controller 350 can selectively activate or deactivate the heating element 346 based on different types of information regarding the drug delivery device 302, including operational state information, condition information, and/or identity information, in accordance with one or more of the methods described above. In some embodiments, the heating element 346 may include an electrically conductive coil that is wrapped around the exterior of the reservoir 312. In other embodiments, the heating element may include an electrically conductive coil wrapped around the cannula 314. Alternatively, or additionally, a cooling element (not illustrated) may be coupled to the reservoir 312 and controllable by the controller 350 in a manner similar to the heating element 346.

The drug delivery device 302 may also include an output unit 347 coupled to the housing 310 and configured to notify the patient or user of information related to the drug delivery device 302. The output unit 347 may be coupled to the controller 350 so that the controller 350 can selectively activate or deactivate the output unit 347 based on different types of information regarding the drug delivery device 302, including operational state information, condition information, and/or identity information, in accordance with one or more of the methods described above. The output unit 347 may be any device suitable for conveying information to the patient or user including a display (e.g., a liquid crystal display), a touchscreen, a light (e.g., a light emitting diode), a vibrator (e.g., an electro-mechanical vibrating element), a speaker, and/or an alarm, among other devices.

The drug delivery device 302 may also include an input unit 348 coupled to the housing 310 and configured to allow a user or patient to input information (e.g., password information) to be used by the controller 350. In some embodiments, the input unit 348, the output unit 347, and even the fingerprint sensor 365, may be a single device such as a touchscreen. In other embodiments, the input unit 348 may be a separate device from the output unit 347 such as a keyboard or button.

As illustrated in FIG. 3, the reservoir 312, the biasing element 324, the locks 328, 335, 341, the plunger 331, the stopper 332, and the drive 330, and the heating element 346 are disposed within the housing 310, along with at least part of the delivery cannula 314. Also disposed within the housing 310 is a controller 350, a communication module 352 (e.g., a wireless transmitter), and at least one sensor or switch. According to the embodiment illustrated in FIG. 3, four sensors are included: a temperature sensor 360, a skin sensor 362, at least one orientation sensor 364, and a fingerprint sensor 365. The sensors 360, 362, 364, and 365 may each generate sensor data (e.g., raw or unprocessed data) related to a respective measured property or aspect of the drug delivery device 302. The sensor data may be representative of at least one of a condition or operational state of the drug delivery device 302. Additionally, the drug delivery device 302 includes a switch 366. The controller 350 is coupled to the communication module 352, the locks 328, 335, 341, the sensors 360, 362, 364, 365, the heating element 346, the fingerprint sensor 365, the output unit 347, the input unit 348, and the switch 366. The controller 350 may be configured to process the sensor data generated by the sensors 360, 362, 364, and 365 to determine a condition and/or operational state of the drug delivery device 302. The controller 350, the communication module 352, one or more of the sensors 360, 362, 364, 365 and the switch 366 may be packaged together as a single module, or each component may be fabricated separately and coupled once the components are disposed within the housing 310. According to certain embodiments, each electrical component may be integrated into the structure of the device 302 associated with that electrical component (e.g., the sensors 362 and 364 may be integrated into the shield 322). In some embodiments, the controller 350, the communication module 352, one or more of the sensors 360, 362, 364, 365, and/or the switch 366 may be packaged together inside the removable sterile barrier 344.

The controller 350 may include at least one processor 370 (e.g., a microprocessor) and a memory 372 (e.g., a random access memory (RAM), a non-volatile memory such as a hard disk, a flash memory, a removable memory, a non-removable memory, etc.). The controller 350 may also include or be coupled to a power supply, e.g. a battery. The processor 370 may be programmed to carry out the actions that the controller 350 is adapted to perform and the memory 372 may include one or more tangible non-transitory readable memories having executable, computer-readable, non-transitory instructions stored thereon, which instructions when executed by the at least one processor 370 may cause the at least one processor 370 to carry out the actions that the controller 350 is adapted to perform. Alternatively, the controller 350 may include other circuitry that carries out the actions that the controller is adapted to perform.

The memory 372 may store the identity information discussed above. The identity information may be stored in the memory 372 prior to the start of execution of any of the methods discussed above. The identity information may include, by way of example and not by way of limitation, a unique identifier, the name of the drug, the dosage, an expiration date, and information regarding the identity of the patient for whom the drug was prescribed. With this information, the controller 350 or a local computing device (e.g., a smartphone) may make a determination regarding the patient that is about to receive the drug, and provide appropriate informational and/or instructional prompts. As an alternative to memory 372, the identity information may be contained in a QR code label or RFID tag associated with the drug delivery device 302.

The communication module 352 may be any of a number of different communication modules used to communicate with a local computing device (e.g., a smartphone) and/or a remote computing device (e.g., a server operated by the device manufacturer). According to one embodiment, the communication module 352 may be a Bluetooth and/or Bluetooth Low Energy module that is on-board with the controller 350. The communication module 352 is used to transmit information from the drug delivery device 302 to the local computing device 304. Alternatively, other wireless protocols may be used by the communication module 352, such as radio-frequency identification (RFID), Zigbee, Wi-Fi, near field communication (NFC), and others. In fact, the communication may be sent along a hardwired connection, rather than using the electromagnetic (EM) spectrum. As defined herein, a communication transmitted and/or received between the module 352, the local computing device, and/or the remote computing device may be in the form of a hardwired signal or EM signal or a pattern of such signals, for example.

The temperature sensor 360 may be disposed proximate to the reservoir 312 so that the temperature of the drug in the reservoir 312 may be determined. Alternatively, the temperature sensor 360 may simply be disposed in the housing 310, so that an approximate temperature of the drug in the reservoir 312 and of the drug delivery device 302 generally may be determined. According to an embodiment, the temperature sensor 360 may be an on-board temperature sensor 360 attached to the processor 370.

The skin sensor 362 may be attached to or associated with the shield 322 to determine when the drug delivery device 302 is disposed on or against the patient's skin. According to one embodiment, the skin sensor 362 is a pressure sensor. According to other embodiments, the skin sensor 362 may be a capacitance sensor, resistance sensor, or inductance sensor. The skin sensor 362 or the switch 366 (which is attached to or associated with the actuator 340) may be used to determine when the drug delivery device 302 is activated or actuated, depending on the design and operation of the drug delivery device 302 that is used to actuate the drive 330, in accordance with the discussion above. It may also be the case that a signal from the skin sensor 360 is used to determine that the drug delivery device 302 has been activated even when the shield 322 is not used as the actual actuator, the underlying assumption being that the movement of the shield 322 is necessarily related to the actuation of the device 302.

The orientation sensors 364, of which there may be at least two as illustrated, may be associated with the shield 322 (or that portion of the housing 310 adjacent the shield 322) and the controller 350 (which may be, as illustrated, disposed at the other end of the drug delivery device 302 or the housing 310 from the shield 322). The orientation sensors 364 may be magnetometers, for example. In particular, the orientation sensor 364 associated with the controller 350 may be an on-board magnetometer. The orientation sensors 364 may be used to determine the orientation of the drug delivery device 302 (in particular, the housing 310) relative to the injection site (or more particularly, relative to the placement of the drug delivery device 302 on or against the patient's skin).

Figure 4:
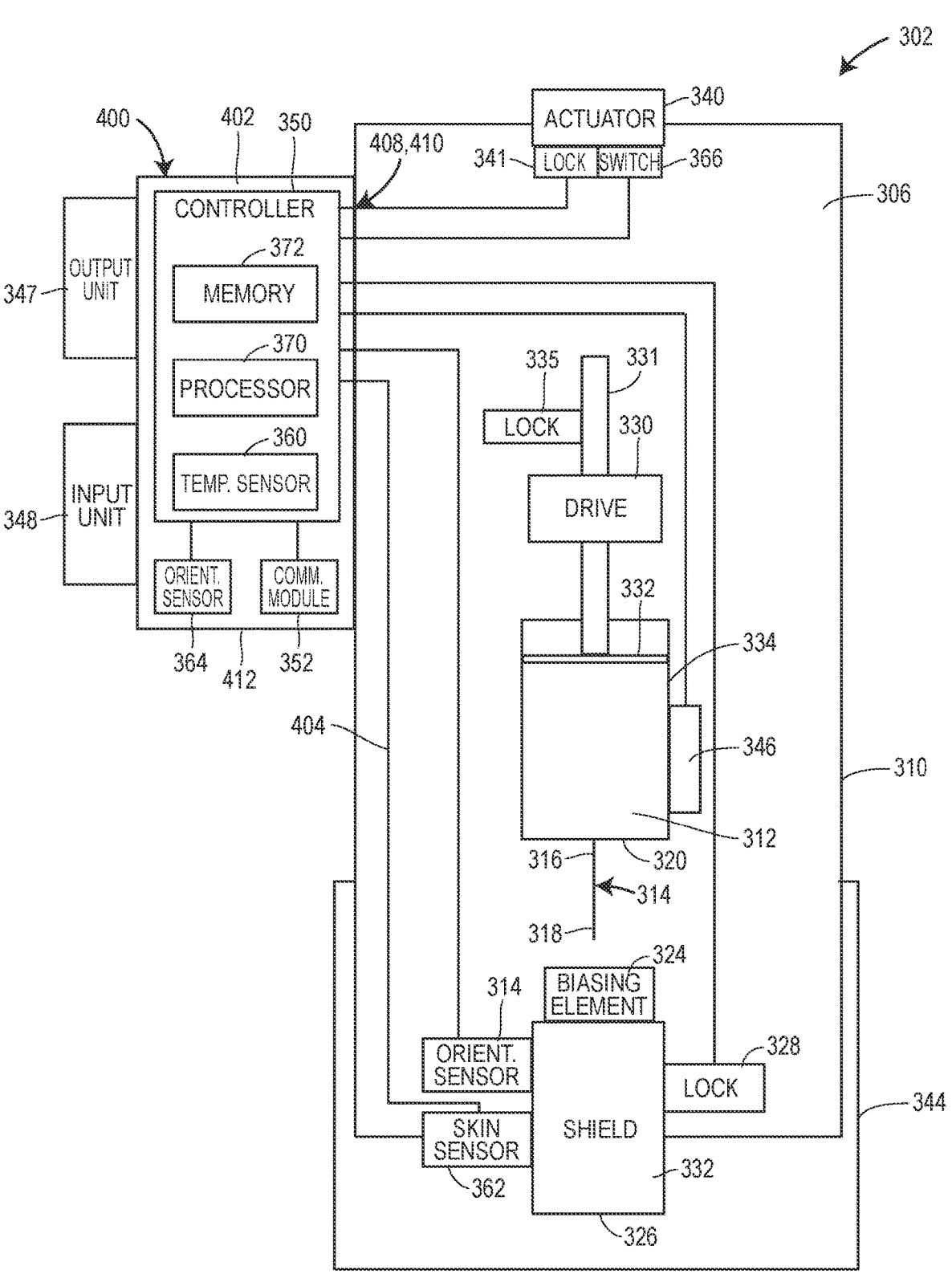
FIG. 4 is a schematic illustration of a drug delivery device with an attachable controller that may be used in the interactive drug delivery system of FIG. 3.

It will be recognized that the arrangement of the components of the drug delivery device 302 within the housing 310 is but one embodiment of this disclosure. For example, FIG. 4 illustrates a second embodiment of the drug delivery device 302, wherein certain components of the drug delivery device 302 are disposed outside the drug delivery device 302.

According to this embodiment, the drug delivery device 302 may include the housing 310, the reservoir 312, the needle 314, the shield 322, the biasing element 324, the lock 328, the drive 330, and the button 340. Furthermore, the sensors 362, 364 and the switch 366 may be disposed within the housing 310. A separate module 400 is provided within a housing 402 in which the controller 350, communication module 352, and on-board temperature and orientation sensors 360, 364 are disposed. The fingerprint sensor 365, the output unit 347, and the input unit 348 may be disposed on the exterior of the module 130 so that a user or patient can interact with them. In some embodiments, the communication module 352 may be disposed within the housing 310 rather than within the module 400.

The module 400 may be adapted to be attached to an exterior surface 404 of the housing 310; for example the module 400 may have an annular or C-shape with a central aperture sized so that an end 406 of the drug delivery device 302 may be disposed within the aperture, and the module 400 held in place by the mating geometries. According to certain embodiments, the module 400 may be moveable relative to the drug delivery device 302, such that movement of the module 400 relative to the housing 310 may activate the autoinjector (e.g., by depressing the button 340), in which case the switch 366 may actually be disposed within the housing 402 of the module 400. According to other embodiments, the exterior surface 404 of the housing 310 and the module 400 may have cooperating connectors. As a further alternative, a fastener may be provided on the housing 310 or the module 400 that cooperates with a feature of the other of the housing 310 or the module 400 to attach or secure the module 400 to the housing 310, whether reversibly or irreversibly. One example of such a fastener may be a set screw on the module 400 that cooperates with a recess on the surface 404 of the housing 310.

The exterior surface 404 of the housing 310 may also have one or more contacts 408 that mate with contacts 410 on an exterior surface 412 of the housing 402 of the module 400. The mating contacts 408, 410 couple the sensors 362, 364, the locks 328, 335, 341, the heating element 346, and the switch 366 inside the drug delivery device 302 with the controller 350 inside the module 400 (i.e., the sensors 362, 364, the locks 328, 335, 341, the heating element 346, and the switch 366 are coupleable with the controller 350, as may be the communication module 352 according to the certain embodiments described above wherein the module 352 is disposed in the housing 310 as well). The contacts 408, 410 may contact each other, or the contacts may mate without having to physically contact each other, in which case the contacts 408, 410 may be provided below the surfaces 404, 412 of the housings 310, 402.

The separation of the controller 350, communication module 352 and other components into a module 400 may permit the module 400 to be used with multiple instances of the drug delivery device 302. In this regard, the module 400 may be considered to be the reusable portion of the drug delivery device 302/module 400 combination (which may be referred to as the drug delivery device 302 for purposes of this disclosure), while the drug delivery device 302 may be considered to be the disposable portion of the drug delivery device 302. By isolating the more expensive components into the reusable module 400 and the less expensive components (including certain sensors) into the disposable drug delivery device 302, the overall cost of the autoinjector may be optimized. This arrangement of the components in the module 400 and the drug delivery device 302 may also facilitate the manufacture and sterilization of the drug delivery device 302 and module 400.

Returning to FIG. 3, the local computing device 304 may be in the form of at least one computing device including at least one processor 420 (e.g., microprocessor) and a memory 422 (e.g., a random access memory (RAM), a non-volatile memory such as a hard disk, a flash memory, a removable memory, a non-removable memory, etc.). The at least one processor 420 and the memory 422 may be incorporated into a controller 423 of the local computing device 304 and/or may be configured separately. Likewise, the remote computing device 306 may be in the form of at least one computing device including at least one processor 424 (e.g., microprocessor) and memory 426 (e.g., a random access memory (RAM), a non-volatile memory such as a hard disk, a flash memory, a removable memory, a non-removable memory, etc.). The at least one processor 424 and the memory 426 may be incorporated into a controller 427 of the local computing device 304 and/or may be configured separately. The processors 422, 424 may be programmed to carry out actions described below relative to the methods of FIGS. 6, 13, and 14, and the memories 422, 426 may include one or more tangible non-transitory computer-readable memories having computer-executable instructions stored thereon (for example, in the form of a custom Mobile Application, or an App for short, or other software module), which instructions when executed by the processors 422, 424 may cause the processors 422, 424 to carry out the actions described below relative to the methods of FIGS. 6, 13, and 14. Alternatively, the local computing device 304 and the remote computing device 306 may include other circuitry that carries out the actions described below relative to the method of FIGS. 6, 13, and 14.

Figure 6:
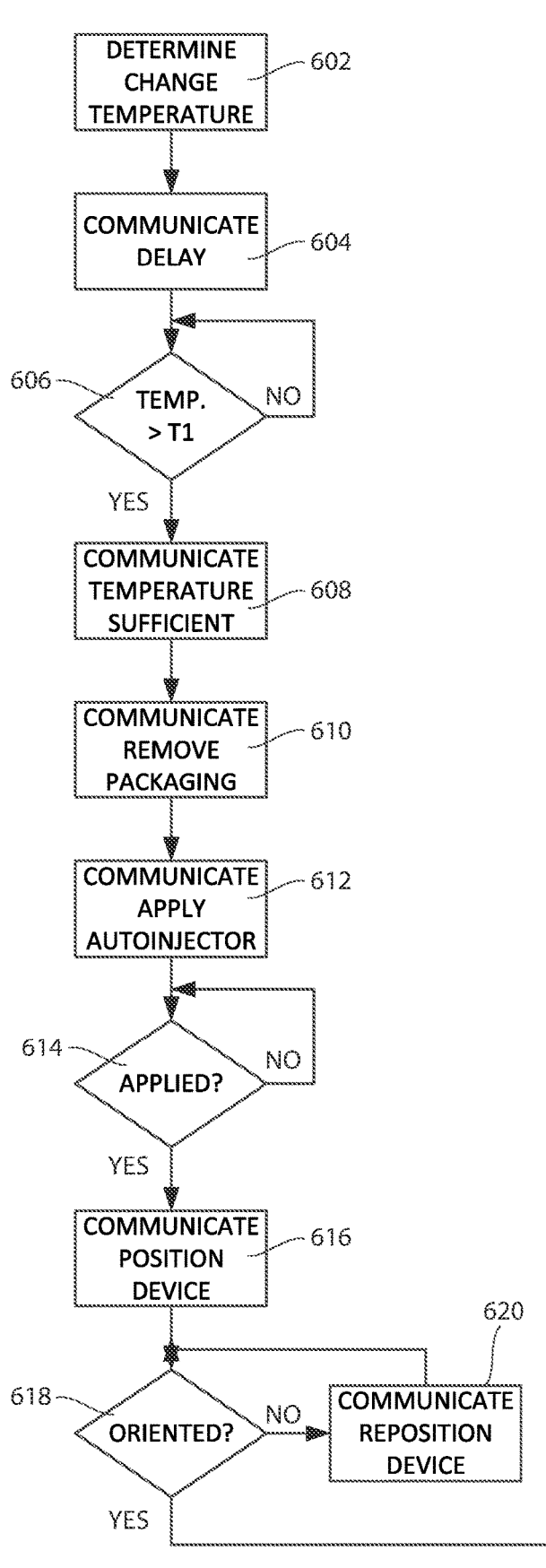
FIG. 6 is a flowchart illustrating the operation of the interactive drug delivery system according to FIG. 3.
Figure 6:
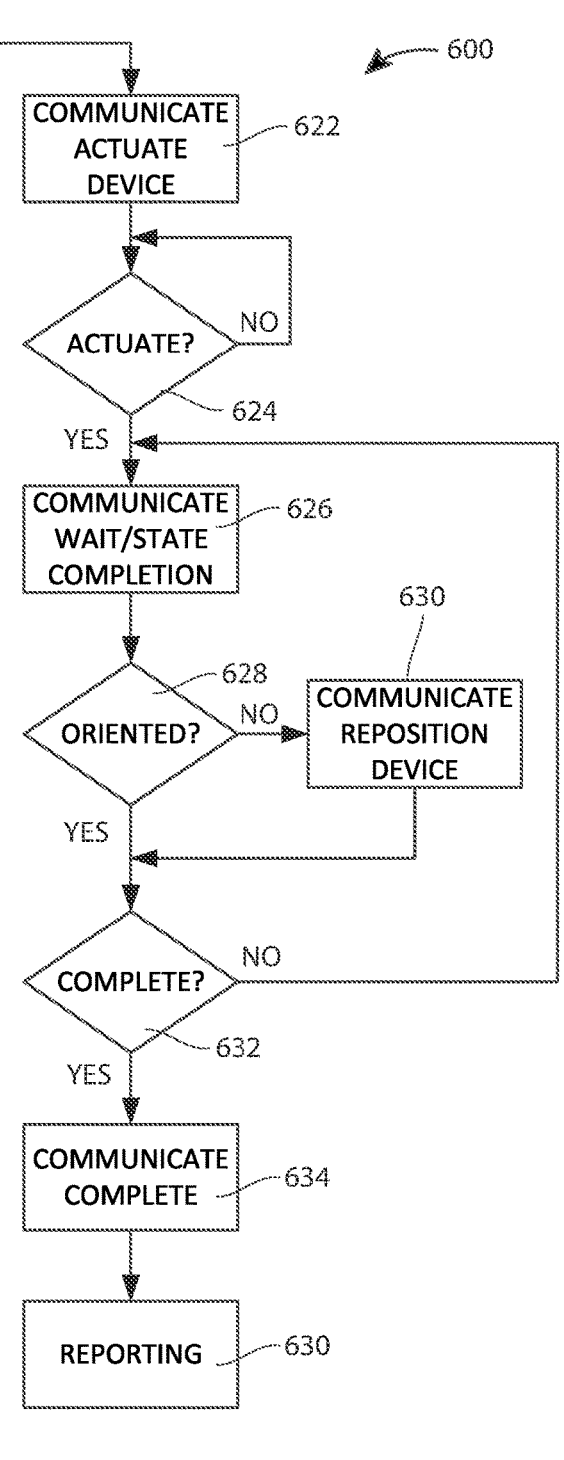
Figure 13:
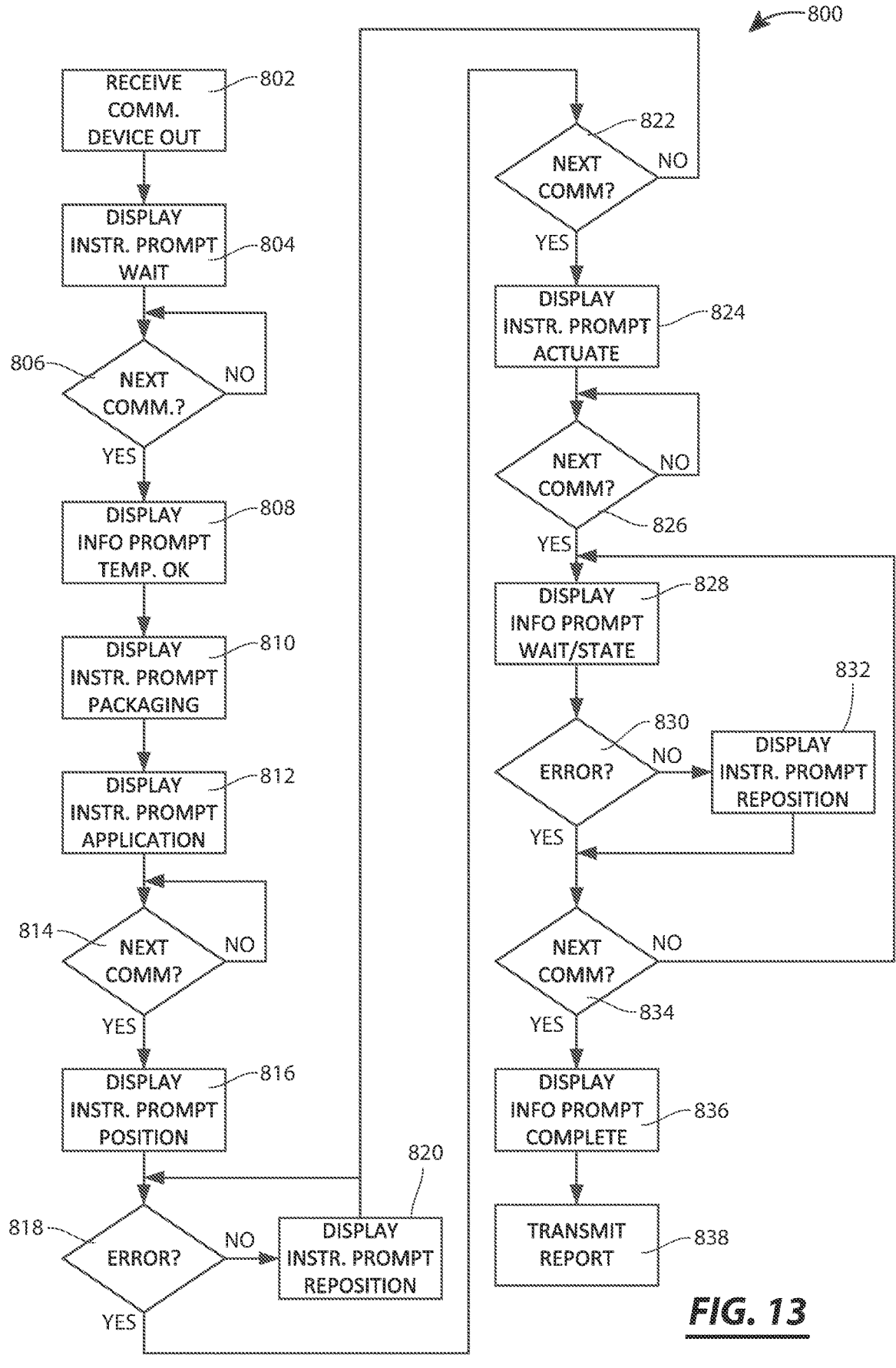
FIG. 13 is a flowchart illustrating the operation of the local computing device of the system of FIG. 3.
Figure 14:
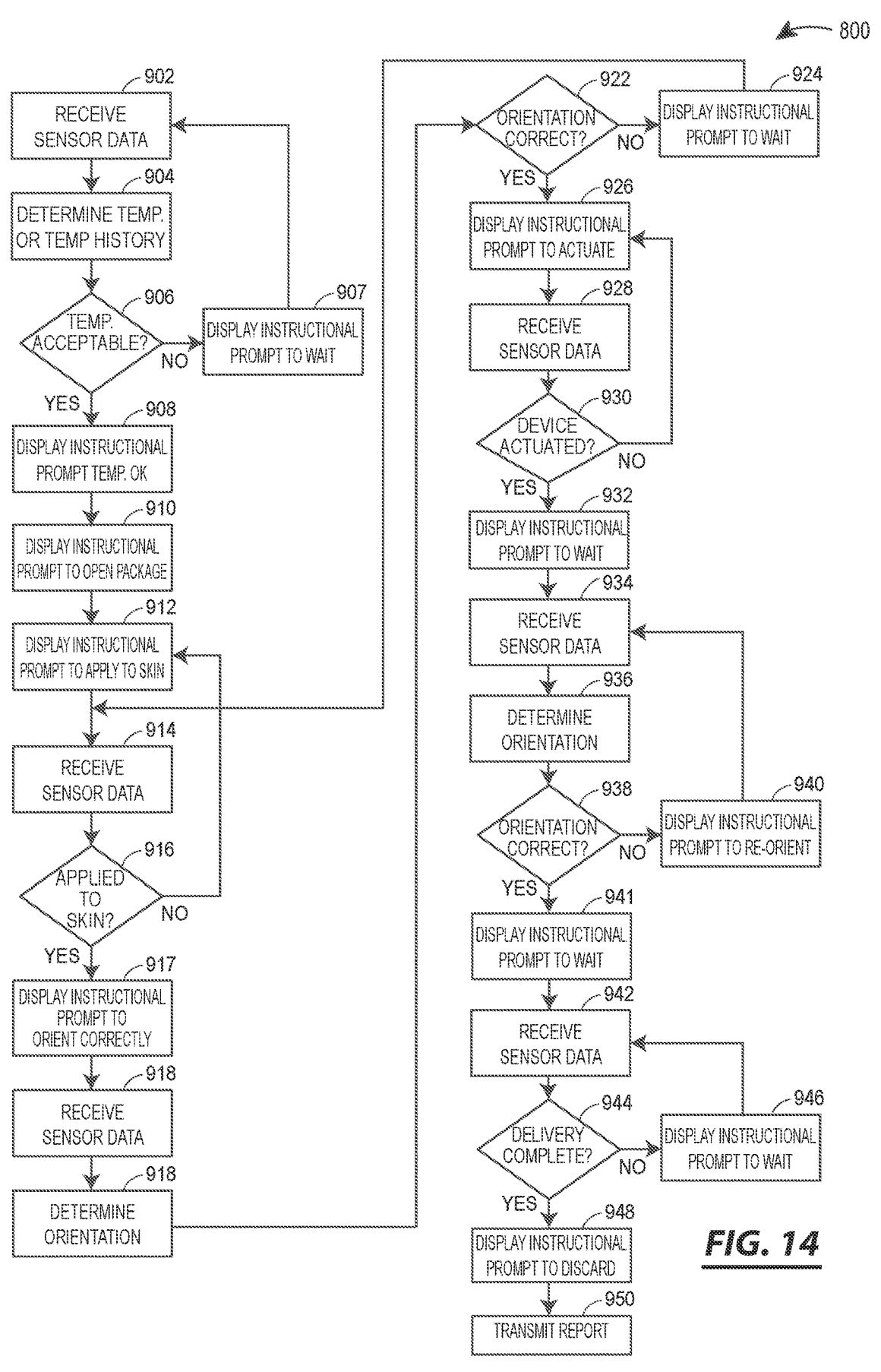
FIG. 14 is a flowchart illustration the operation of the local computing device according to another embodiment.

In fact, according to certain embodiments of this disclosure, the local computing device 304 may carry out the actions of FIGS. 6, 13, and 14 independent of the remote computing device 306. According to other embodiments, the local computing device 304 may carry out certain of the actions of FIGS. 6, 13, and 14, while the remote computing device 306 carries out other of the actions of FIGS. 6, 13, and 14. For example, according to certain embodiments the processor(s) 420 may control components of the local computing device 304 permitting communication with the controller 350 and/or the user, but may not make the determinations as to the content of those communications, the determinations relative to the content of the communications being made at the remote computing device 306.

According to the illustrated embodiment, the local computing device 304 is a mobile computing device (e.g., a smartphone, smartwatch, tablet computer, etc.) while the remote computing device 306 is a server. In some embodiments, the local computing device 304 can include generally any computing device capable of processing data and being synched to and in communication with the drug delivery device 302 such as, for example, a smart wearable device, a personal computer, a laptop computer, a smart television, a smart appliance, a smart automobile, a networked computer, etc. According to other embodiments, the local computing device 304 may be a dedicated device such as a hub or gateway that can establish a communication link with the communication module 352 and potentially the remote computing device 306, where communication with the remote computing device 306 is necessary or desirable.

To carry out the actions of the methods described in FIGS. 6, 13, and 14, the local computing device 304 may further include a communication module 430 for wireless communication with the communication module 352 of the drug delivery device 302, for example by using Bluetooth/Bluetooth Low Energy protocol. Alternatively, other wireless protocols may be used by the communication module 352, such as radio-frequency identification (RFID), Zigbee, Wi-Fi, near field communication (NFC), cellular, and others. The local computing device 304 may also include a display 432 to be used to communicate instructions to the user. The local computing device 304 may include other output devices other than the display 432 to communicate with the user, such as a speaker 434 for example. The speaker 434 may be controlled by the processor(s) 420 to provide an audible form of the instructions displayed in written form on the display 432.

The local computing device 304 may also include one or more communication modules, which may be the same as or different from the communication module 430, that may be used to communicate with one or more networks 440, 442. For example, the network 440 may be a wireless radio frequency network, such as a cellular mobile device network, while the network 442 may be a network of computing devices, such as the Internet. As is illustrated in FIG. 6, the networks 440, 442 may be in communication with each other, such that the local computing device 304 may communicate with the remote computing device 306 over the network 440, the network 442 or a combination of the networks 440, 442. The remote computing device 424 may include a communication module 436 to receive communications from the networks 440, 442.

While the terms "local" and "remote" have been used to describe the local computing device 304 and the remote computing device 306, these terms have not been selected to require a particular spatial or geographical distance between the devices 304, 306. Instead, the terms have been used to suggest a relative proximity to the user, and the fact that the remote computing device 306 is not required to be at the same physical location as the user and the drug delivery device 302. According to certain embodiments, it is possible, even likely, that the remote computing device 306 may be located in a different geographic location than the user and the drug delivery device 302, for example a different city, state or country.

The local computing device 304 and the remote computing device 306 are each separate from, and spaced apart from, the drug delivery device 302 and therefore may each be considered to be an "external computing device" relative to the drug delivery device 302.

Figure 5:
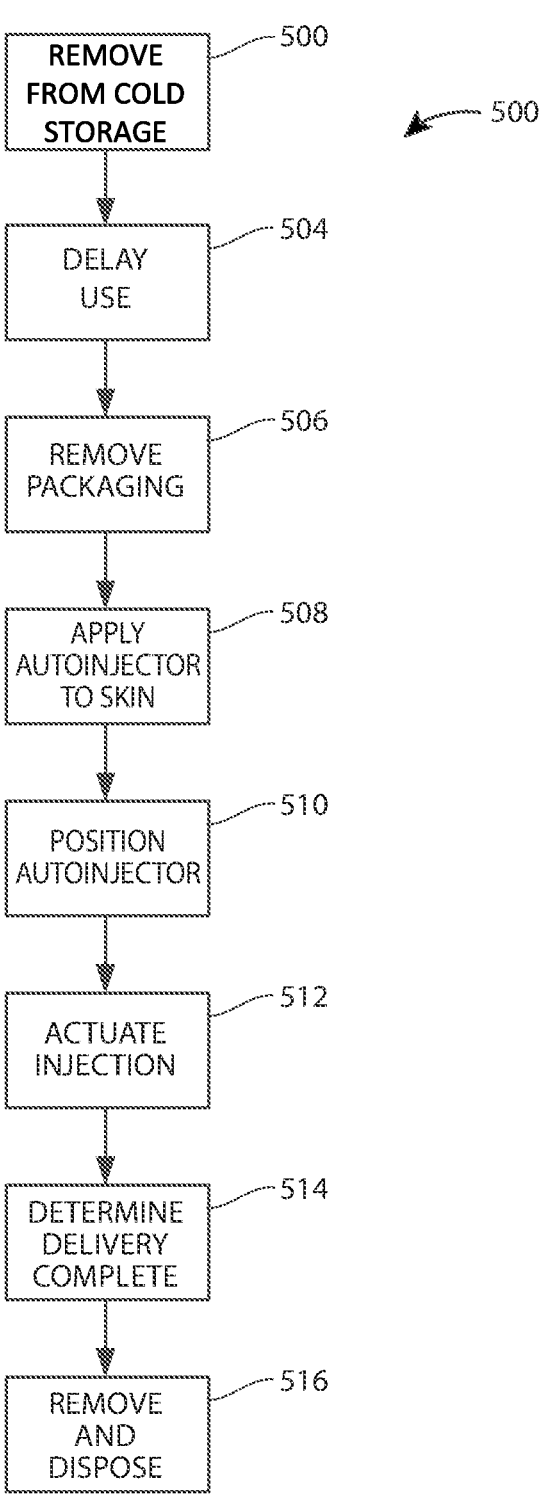
FIG. 5 is a flowchart illustrating the operation of the drug delivery device according to FIG. 3.

Before describing the interaction and communication of information between the drug delivery device 302, the local computing device 304, and the remote computing device 306, a method 500 of operating the drug delivery device 302 is described with reference to FIG. 5. The method 500 begins at block 502 with the removal of the drug delivery device 302 from cold storage, such as a refrigerator. Because the medicament in the reservoir 312 is cold, it is desirable to delay use at block 504 for some period of time after the drug delivery device 302 is removed from cold storage to permit the device 302 and the drug to warm. The warming of the device 302 and the drug may improve the performance and reliability of the operation of the device 302 and/or the delivery of the drug. Alternatively, the warming of the device 302 and the drug may be to minimize discomfort associated with delivery of the drug when cold. In any event, after a delay at block 504, the method 500 continues to block 506. While this description applies to removal of an auto-injector from cold storage, it should be apparent that the method can apply equally well to whether the device is too warm when removed from storage.

At block 506, the packaging is removed from about the drug delivery device 302. For example, a removable, disposable cover may be disposed over the second end 318 of the needle 314 during storage to preserve sterility and prevent accidental contact. This cover may be removed by the user prior to placement and actuation of the device, as well as any other packaging that limits or prevents the use of the device (e.g., an external safety lock). Once the packaging is removed at block 506, the drug delivery device 302 is applied to the patient's skin at block 508. The drug delivery device 302 is then positioned in a particular orientation to the body of the patient at block 510.

With the drug delivery device 302 on or against the skin and in the correct position, the user is ready to actuate the drug delivery device 302 at block 512. For example, the user may depress the button 340 or press the drug delivery device 302 in the direction of the skin, causing relative motion between the housing 310 of the drug delivery device 302 and the shield 322, which relative motion actuates the device. Having actuated the drug delivery device 302, the user waits for the completion of the delivery at block 514.

The completion of the delivery of the drug by the drug delivery device 302 may be signaled to the user in a number of different ways. For example, the drug delivery device 302 may have a window in the side of the housing 310 that permits visualization of the reservoir 312, and in particular the movement of the stopper 332 along the bore 334 of the reservoir 312. As an alternative, the drug delivery device 302 may include a noise-making device, such as a ratchet or clicker, that actuates when the drug delivery is complete. Once the delivery is complete, the drug delivery device 302 may be removed and disposed of at block 516.

As mentioned above, a user (which may be the patient or alternatively the health care provider) may have difficulty with any or all of the steps of the method 500. For example, the user may be uncertain whether to delay use (block 504) or how long to delay use. Alternatively, the user may not apply the device 302 against the skin (block 508) or the drug delivery device 302 may be improperly positioned (block 510). The user may be uncertain how to determine that delivery is complete (block 514) and thus may administer less than the entire dose. The user may confuse the sequence of steps outlined in the method 500, or may simply forget to or decide not to perform any of the steps of the method 500.

Referring to FIG. 6, a method 600 is provided for using the interactive drug delivery system 300 to limit the likelihood that the user will fail to carry out the steps of the method 500. While the method 600 describes the operation of the entire system 300, further methods are provided in FIGS. 12 and 13 that may be carried out by the controller 350 of the drug delivery device 302, the local computing device 304, and/or the remote computing device 306. Method 600 is also discussed with reference to the simulated screenshots of FIGS. 7-11.

The method 600 begins at block 602, wherein the system 300 determines that the drug delivery device 302 has been removed from cold storage. In particular, the temperature sensor 360 is used to determine that a temperature change has occurred relative to the drug delivery device 302, in particular an increase in temperature. This change in temperature is communicated from the drug delivery device 302 to the local computing device 304, which is operating software, such as a Mobile Application, that permits this information to be received from the drug delivery device 302 and used to generate a series of instructions and information prompts for the user which are displayed on the display 432 of the local computing device 304, as illustrated in FIGS. 7-11. According to certain embodiments, the local computing device may control the display 432 to display instructions or informational prompts not only according to the communication received, but also according to information stored on the local computing device 304 or received by the local computing device 304 (i.e., other than the communication). According to the method 600, a first instructional prompt may be displayed by the local computing device 304 at block 604 that the user should wait before proceeding with the operation of the device (see FIG. 7).

The method 600 then continues at block 606, wherein the temperature sensor 360 is monitored to determine if the temperature of the drug delivery device 302 has increased above a desired threshold (i.e., T1). If the temperature has not increased above the threshold, the system 300 continues to monitor the temperature at block 606. Otherwise, the method 600 continues to block 608, wherein a further instructional prompt may be displayed by the local computing device 304 that the user may proceed with the operation of the drug delivery device 302 (see FIG. 8).

The method 600 may then continue with additional instructional prompts displayed by the local computing device 304 at blocks 610, 612 for the user to remove any packaging (e.g., a needle cover) and to apply the drug delivery device 302 to the patient's skin. The system 300 then monitors the skin sensor 362 to determine if the drug delivery device 302 has been applied to the skin at block 614. If the drug delivery device 302 has not been applied, then the method 600 remains at block 614; if the drug delivery device 302 has been applied, then the method 600 continues to block 616.

At block 616, a further instructional prompt may be displayed by the local computing device 304 that the user should position the drug delivery device 302 on the skin. For example, it may be desirable for the drug delivery device 302 to be positioned on the skin such that the needle 314 will enter the skin at a right angle or orthogonally to the skin. The system 300 may use the orientation sensors 364 to monitor the orientation of the device at block 618, and further instructional prompts may be displayed by the local computing device 304 for the user to alter the position of the device 302 relative to the skin at block 620. See FIG. 9. Once the system determines that the position of the drug delivery device 302 is acceptable, the method may proceed to block 622.

At block 622, an instructional prompt may be displayed by the local computing device 304 that the user should actuate the drug delivery device 302. The system 300 may then monitor the switch 366 to determine that the user actuates the button 340, before continuing to block 626. At block 626, an instructional prompt may be displayed by the local computing device 304 that the user should wait for completion of the drug delivery. See FIG. 10. Also at block 626, the local computing device 304 may display informational prompts letting the user know that a certain amount of the drug has been delivered. See also FIG. 10. This informational prompt may depend on determinations made based on additional sensors that, for example, monitor the travel of the stopper 332 in the bore 334 of the reservoir 312. Alternatively, the informational prompt may be based on an estimate of the completion state based on timed trials performed using other instances of the drug delivery device 302 with the drug being delivered or administered.

At the same time, the system 300 may continue to monitor the orientation sensors 364 at block 628 to determine that the drug delivery device 302 remains in position relative to the patient's skin. Instructional prompts to reposition the drug delivery device 302 may be displayed by the local computing device 304 per block 630 in addition to or in substitution for the information prompts displayed per block 626. The system 300 also determines if the drug delivery is compete at block 632, which determination may be made based on monitoring of sensors, e.g., associated with the stopper 332, or based on estimates based on timed trials, for example. In fact, the determinations made at blocks 628 and 632 may be combined, with the instructional prompt displayed per block 630 occurring only if the autoinjector should be repositioned and the delivery is not complete.

Once the system 300 determines that the drug delivery is complete, the method 600 continues to block 634, where an informational prompt may be displayed by the local computing device 304 that the delivery is complete and that the device may be removed and disposed of (see FIG. 11), and block 636, where a report of the completion of the drug delivery by the user using the drug delivery device 302 is provided, for example, to the remote computing device 306.

As mentioned above, the method 600 describes the operation of the entire system 300. However, the operation of the entire system 300 may also be described in terms of the actions performed by the drug delivery device 302 and the local computing device 304. The individual operations of each device 302, 304, and the cooperation between the devices 302, 304, is now described with reference to FIGS. 12 and 13. It should be noted that, in an alternative embodiment, some or all of the actions performed by the local computing device 304 with regard to FIG. 13 may be performed by the remote computing device 306.

Figure 12:
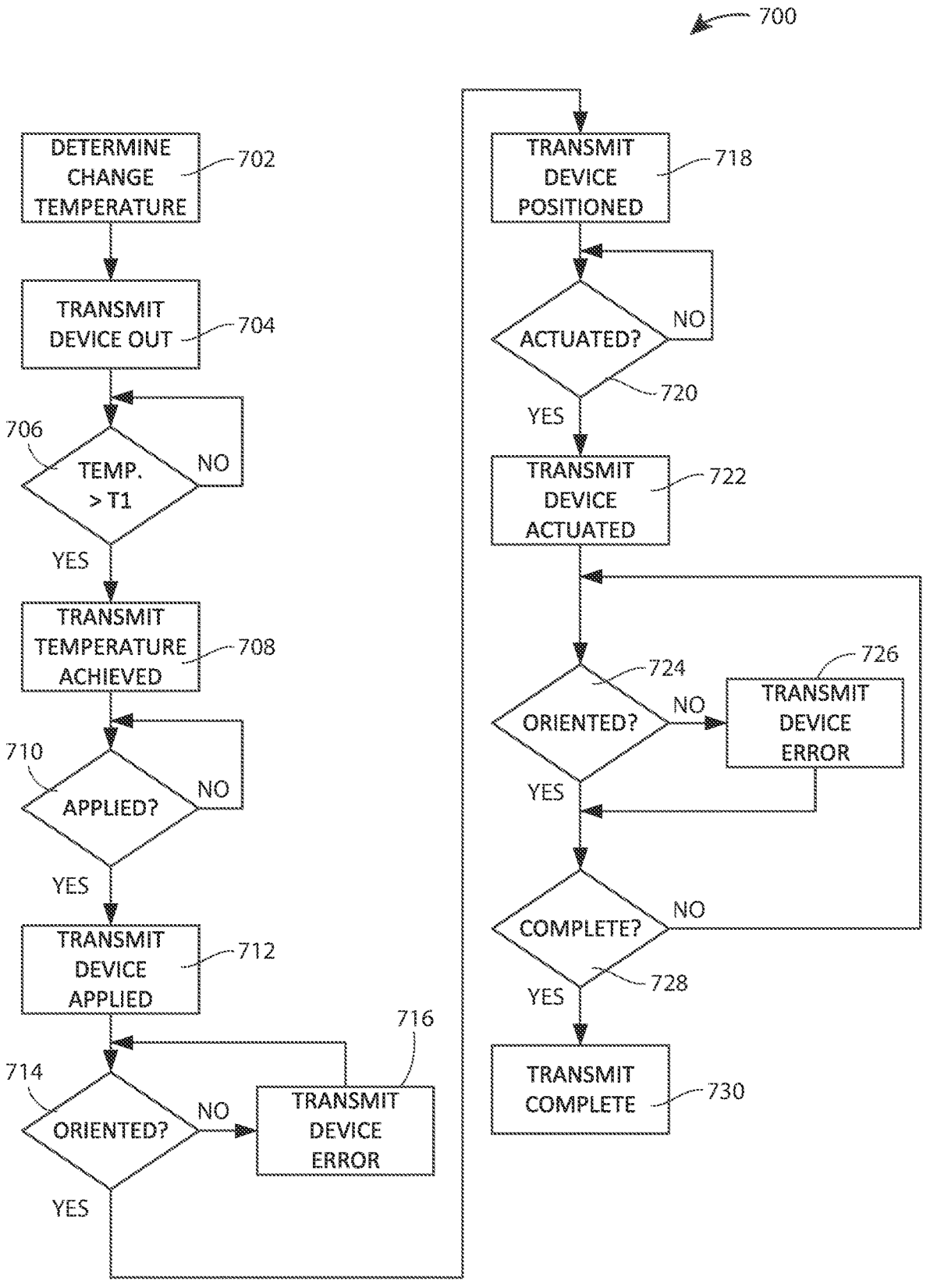
FIG. 12 is a flowchart illustrating the operation of the controller associated with the drug delivery device of the system of FIG. 3.

With reference first to FIG. 12, a method 700 is provided relative to the operation of the controller 350. The method 700 begins at block 702, with the controller 350 monitoring the temperature sensor 360 to determine if the drug delivery device 302 has been removed from cold storage. When the controller 350 determines that the temperature has increased, corresponding to a probable removal from cold storage, the controller 350 controls the communication module 352 to transmit a communication (in the form of a signal) at block 704 to the local computing device 304 that the autoinjector 304 has been removed from cold storage.

With reference now to FIG. 13, a method 800 carried out by the local computing device 304 starts at block 802 with the receipt by the local computing device 304 (or more particularly, the communication module 430) of the communication transmitted by the drug delivery device 302 (or more particularly, the communication module 352) that the drug delivery device 302 has been removed from cold storage. The method 800 continues to block 804, where the processor 420 of the controller 423 controls the display 432 to display an instructional prompt to the user instructing the user to wait before using the drug delivery device 302. Prior to displaying the instructional prompt at block 804, the processor 420 of the controller 423 may process (e.g., compare) the communication received from the drug delivery device 302 at block 802 with or according to information stored in the memory 422 of the local computing device 304 to determine if the sensed temperature is acceptable for a patient to use the drug delivery device 302. The instructional prompt may be displayed at block 804 in response to a determination that the sensed temperature is not acceptable for a patient to use the drug delivery device 302. Subsequently, at block 806, the local computing device 304 (or more particularly, the processor 420) may monitor the module 430 for the next communication from the drug delivery device 302.

Returning to FIG. 12, method 700 continues with the controller 350 monitoring the temperature sensor 360 at block 706 to determine when the temperature sensed by the temperature sensor 360 exceeds a threshold temperature. When the controller 350 determines that the sensed temperature exceeds a threshold temperature, the controller 350 controls the communication module 352 to transmit a communication to the local computing device 304 that the temperature has been achieved at block 708. In some embodiments, the controller 350 may control the communication module 352 to transmit a communication representative of the temperature of the drug delivery device 302 and, upon receipt, the controller 423 of the local computing device 304 may compare the sensed temperature to information (e.g., threshold temperature information indicating a minimum temperature or temperature range) stored in the memory 422 of the local computing device 304 to determine if the sensed temperature is acceptable for a patient to use the drug delivery device 302.

Upon receipt of a temperature communication at block 806 of FIG. 13, the method 800 continues at block 808, where the processor 420 controls the display 432 to display an informational prompt instructing the user that the temperature of the drug delivery device 302 is now suitable or acceptable for use. The method 800 continues on to blocks 810 and 812, where the processor 420 controls the display 432 to display instructional prompts to the user that the user is to remove any packaging and to apply the drug delivery device 302 to the patient's skin. The method 800 then continues at block 814 to monitor the communication link for the next communication from the drug delivery device 302.

In some embodiments, the controller 350 may evaluate a temperature history of the drug delivery device 302 to determine the range and duration of temperatures experienced by the drug delivery device 302 in the past to determine if the temperature history renders the drug delivery device 302 or its medicament unacceptable for use. If so, the controller 350 may control the communication module 352 to transmit a communication to the local computing device 304 that the temperature history of the drug delivery device 302 renders it unsuitable for use, and the controller 423 of the local computing device 304 controls the display 423 to display an informational prompt instructing the patient not to use the device. In some embodiments, the evaluation of the temperature history may be performed by the controller 423 of the local computing device 304 by comparing temperature history received from the drug delivery device 302 with information stored in the memory 422 of the local computing device 304 to determine if the temperature history is acceptable for a patient to use the drug delivery device 302.

Next, the method 700 continues with the controller 350 monitoring the skin sensor 362 to determine if the drug delivery device 302 has been applied to the patient's skin at block 710 of FIG. 12. When the controller 350 determines that the drug delivery device 302 has been applied to the patient's skin, the controller 350 controls the communication module 352 at block 712 to transmit a communication to the local computing device 304 that the drug delivery device 302 has been applied.

Upon receipt of the communication of skin application, as determined at block 814 of FIG. 13, the method 800 continues to block 816 with the processor 420 controlling the display 432 to display an instructional prompt instructing the user or patient that the drug delivery device 302 must be aligned with respect to the patient's skin. The instructional prompt may include illustrations of the proper manner in which the device is to be positioned relative to the patient's skin. In order to generate the instructional prompt at block 816, the processor 420 may process (e.g., compare) the communication received from the drug delivery device 302 at block 814 with or according to information stored in the memory 422 of the local computing device 304.

The method 800 may then proceed to block 818, wherein the processor 420 monitors the communication link for any error communications received from the drug delivery device 302 regarding the position and/or orientation of the device (see blocks 714, 716 of method 700 of FIG. 12), and controls the display 432 to display an instructional prompt to the user at block 820 if an error communication is received. The error communication may include an indication of the type of positional and/or orientation error occurring, such that the instructional prompt displayed may be tailored to provide specific guidance (e.g., "Tilt Right" or "Tilt Left"). In order to generate the instructional prompt at block 820, the processor 420 may process (e.g., compare) the error communications received from the drug delivery device 302 at block 818 with or according to information stored in the memory 422 of the local computing device 304. The method 800 further continues to block 822, with the processor 420 monitoring the communication link for a further communication from the drug delivery device 302 and cycling between blocks 818, 822 until such a further communication is received.

As reflected in FIG. 12, the controller 350 is monitoring the orientation sensors 364 at this time to determine if the drug delivery device 302 is properly oriented at block 714. The controller 350 will control the communication module 352 to transmit one or more error communications at block 716 if the position of the device 302 is incorrect, and a device positioned communication at block 718 when the device 302 is correctly positioned. In some embodiments, the controller 350 may control the communication module 352 to transmit a communication representative of the orientation of the delivery device 302 and, upon receipt, the controller 423 of the local computing device 304 may compare the sensed orientation with information stored in the memory 422 of the local computing device 304 to determine if the sensed orientation is acceptable for a patient to use the drug delivery device 302 to delivery its medicament to the patient.

Upon receipt of the correct position communication, as determined at block 822 of FIG. 13, the method 800 continues at block 824 with the processor 420 controlling the display 432 to display an instructional prompt to the user to actuate the drug delivery device 302, starting the delivery of the drug. In order to generate the instructional prompt at block 822, the processor 420 may process (e.g., compare) the communications received from the drug delivery device 302 at block 822 with or according to information stored in the memory 422 of the local computing device 304. The method 800 then continues to block 826, where the processor 420 monitors the communication link for the next communication from the drug delivery device 302.

At the same time, the controller 350 is monitoring the switch 366 to determine if the button 340 has been depressed, or if other action has been taken to actuate the drug delivery device 302, as indicated at block 720 of FIG. 12. Once the controller 350 has received a signal from the switch that the button 340 has been depressed, for example, the controller 350 controls the communication module 352 to transmit a device actuated communication to the local computing device 304, as indicated at block 722.

Upon receipt of the device actuated communication, as determined at block 826 of FIG. 13, the method 800 continues at block 828 with the processor 420 controlling the display 432 to display an informational prompt to the user that the injection has begun. In order to generate the instructional prompt at block 828, the processor 420 may process (e.g., compare) the communications received from the drug delivery device 302 at block 826 with or according to information stored in the memory 422 of the local computing device 304.

The method 800 may continue to blocks 830, 832 where the processor 420 monitors the communication link for any error communication relative to the position of the device (block 830) and controls the display 432 to display an instructional prompt to the user to reposition the device (block 832). See also blocks 724 and 726 of method 700 of FIG. 12. The method 800 further continues to block 834, where the processor 420 monitors the communication link for a further communication from the drug delivery device 302. While illustrated as separate blocks, it will be recognized that the actions of blocks 830 and 834 may be combined in a single block.

Until such communication is received, the method 800 repeats blocks 828, 830, 834 (and as circumstances dictate, block 832). It will be recognized that during repeated iterations of block 828, the processor 420 may control the display 432 to provide informational prompts to the user that reflect progress toward the delivery of the drug from the drug delivery device 302. Consequently, the repetition of block 828 is not intended to indicate that the same informational prompt is repeatedly displayed to the user, although that might be done according to certain embodiments.

Returning to the method 700 of FIG. 12, the controller 350 continues to monitor the orientation sensors 364 at block 724 (and transmit error communications at block 726, as required) until the controller 350 determines that the injection is complete at block 728. While these actions are illustrated as different blocks in FIG. 12, the actions of blocks 724 and 728 may be combined. When the controller 350 determines that the injection is compete at block 728, then the controller 350 controls the communication module 352 to send a delivery complete communication to the local computing device 304 at block 730.

It will be recognized that the determination made at block 728 may be made, as indicated above, based on monitoring of the signals received from one or more sensors associated with the reservoir 312. Alternatively, the determination at block 728 may be made based on a timer set according to an estimate of the time required to eject the drug completely from the reservoir 312 according previously performed time trials. According to other embodiments, the controller 312 may not make the determination that the delivery is complete, but rather this determination may be made by the local computing device 304, for example based on the receipt of the device actuated communication, a timer monitored or maintained by the processor 420, and an estimate of the time required to eject the drug completely from the reservoir 312 according to previously performed time trials.

However, according to the illustrated embodiment, the delivery complete communication is transmitted to the local computing device 304, and the method 800 continues at blocks 834, 836 at FIG. 13 with the receipt of the communication by the local computing device 304 (block 834) and the processor 420 controlling the display 432 to display an informational prompt to the user that the delivery has been completed and/or an instructional prompt to safely discard the drug delivery device 302. The processor 420 may then format and transmit a report indicative of completion of the drug delivery to the patient to the remote computing device 306 regarding the operation of the device 302 at block 838.

While the structure and operation of embodiments of a system 300 according to this disclosure has been discussed above, it will be recognized that further variants of this system 300 and its methods of operation may be described.

For example, while the foregoing suggests that the communications (other than the error communications) carry some identifying information that makes each unique (e.g., the delivery complete communication), this need not be the case according to all embodiments. For example, the local computing device 304 may simply wait for the next non-error communication received from the drug delivery device 302, and on the basis that a further non-error communication has been received, the local computing device may move to the next action of method 800. As such, all of the non-error communications may be indistinguishable from each other.

As an additional example, in addition to the information that is transmitted from the drug delivery device 302 to the local computing device 304 above, the drug delivery device 302 may include in memory 372 identity information regarding the drug and/or the device 302. This identity information may be transmitted to the local computing device 304 before or at the same time the controller 350 controls the communication module 352 to transmit the initial "device out" communication of block 704 of FIG. 12, or with the reporting that occurs at block 636 in FIG. 6. The information may include, by way of example and not by way of limitation, a unique identifier, the name of the drug, the dosage, and the expiration date. Alternatively, this information may be contained in a QR code label or RFID tag associated with the drug delivery device 302, and the local computing device processor 420 may control the display 432 to display an instructional prompt to the user for the user to use the local computing device 304 to obtain this information. In any event, the method 800 of FIG. 13 may include displaying informational prompts to the user based on this information, and even instructional prompts should the local computing device 304 determine that the drug product is not appropriate for use by the user because, for example, the drug is incorrect, the dosage is incorrect, or the expiration date is past due.

Along similar lines, the identifying information may include information regarding the identity of the patient for whom the drug was prescribed. With this information, the local computing device 304 may make a determination regarding the patient that is about to receive the drug, and provide appropriate informational and/or instructional prompts. In conjunction with the drug identity information discussed above, and the local computing device 304 may use this information to address the five Rights in Medication Administration: Right Patient, Right Drug, Right Dose, Right Time, and Right Route.

The local computing device 304 may also operate to display information prompts in the form of reminders to follow the prescribed treatment regimen. In fact, the remote computing device 306 may interact with and/or control one or more local computing devices 304 that display the reminder information prompts. The remote computing device 306 may control the timing and/or content of the displayed reminder information prompts based on information received from the one or more local computing devices 304. For example, the remote computing device 306 may determine that one or another message is best suited for (e.g., most effective with) users where the one or more local computing devices 304 evidence a particular type of use or behavior pattern on the part of these users, and may control the timing and/or content of the reminder information prompts accordingly. Other informational prompts that may be displayed on the local computing device may include personal injection histories, or general educational material regarding efficacy expectations for patients on the prescribed treatment regimen.

By processing communications from the drug delivery device 302 at the local computing device 304 according to the method 800, the data processing and/or storage burden on the drug delivery device 302 may be reduced. Furthermore, the drug delivery device 302 may not be required to have a display for providing informational and/or instructional prompts to the patient or user. Accordingly, the method 800 permits the use of relative simple and/or inexpensive computer hardware onboard the drug delivery device 302, which may be desirable from an economic perspective, especially if the drug delivery device 302 is a disposable, single-use device, or otherwise has a limited lifespan.

To further reduce the data processing and/or storage burden on the drug delivery device 302, the drug delivery device 302 may transmit the sensor data (e.g., raw or unprocessed data) from one or more of the sensors 360, 362, 364, and 365 to the local computing device 304 and/or the remote computing device 306 without processing sensor data, or with very minimal processing of the sensor data, prior to its transmission. Accordingly, in such an embodiment, the local computing device 304 and/or the remote computing device 306, as opposed to the drug delivery device 302, may process the sensor data to determine the condition and/or operational state of the drug delivery device 302. Besides transmitting the sensor data to the local computing device 304 and/or the remote computing device 306, the drug delivery device 302 may not be required to process the sensor data. This configuration may free the drug delivery device 302 from having to include a controller 350, processor 370, and/or memory 372, thereby reducing the cost and complexity of the drug delivery device 302. In such an embodiment, the only computer-related electronics onboard the drug delivery device 302 may be the sensors 360, 362, 364, and 365 and the communication module 430.

An example of a method, designated by reference numeral 900, in which the local computing device 304, as opposed to the drug delivery device 302, processes the sensor data to determine at least one of a condition and/or an operational state of the drug delivery device 302 will now be described with reference to FIG. 14. In some embodiments, some or all of the steps of the method 900 may be performed by the remote computing device 306 instead of the local computing device 304. The method 900 begins at block 902 with the local computing device 304 receiving, at the communication module 430, sensor data generated by the temperature sensor 360 and transmitted from the communication module 352 of the drug delivery device 302. Next, at block 904, the sensor data received at block 902 may be processed (e.g., analyzed) by the processor 420 of the local computing device 304 according to information stored in the memory 422 of the local computing device 304 to determine a temperature or a temperature history of the drug delivery device 302.

The method 900 then continues to block 906 where the processor 430 compares the temperature or temperature history determined at block 904 with information stored in the memory 422 to determine if the temperature or temperature history is acceptable for the patient to use the drug delivery device 302. In some embodiments, the processor 430 may compare the temperature to a threshold temperature and determines that the temperature is acceptable only if the temperature exceeds the threshold temperature. In embodiments where the temperature history is evaluated, the processor 430 may compare the temperature history with an acceptable temperature range to determine if, and how long, the drug delivery device 302 was outside the acceptable temperature range in the past.

In response to a determination that the temperature or temperature history is not acceptable at block 906, the processor 430 may control the display 432 to display an instructional prompt to the user instructing the user to wait before using the drug delivery device 302 (or to never use the drug delivery device if the temperature history is unacceptable, for example) at block 907, and subsequently the method 900 may return to block 902. In response to a determination that the temperature or temperature history is acceptable at block 906, the processor 430 may control the display 432 to display instructional prompts instructing the user that the temperature or temperature history of the drug delivery device 302 is acceptable for use, to remove any packaging from the drug delivery device, and to apply the drug delivery device 302 to the patient's skin, at, respectively, blocks 908, 910, and 912.

Subsequently, the method 900 continues on to block 914, where the local computing device 304 receives, at the communication module 430, sensor data generated by the skin sensor 362 and transmitted from the communication module 352 of the drug delivery device 302. Next, at block 916, the sensor data received at block 914 may be processed (e.g., analyzed) by the processor 420 of the local computing device 304 according to information stored in the memory 422 of the local computing device 304 to determine if the drug delivery device 302 is disposed on or against a skin of the patient. In response to a determination that the drug delivery device 302 is not applied to the patient's skin at block 916, the method 900 may return to block 912. In response to a determination that the drug delivery device 302 is applied to the patient's skin at block 916, the processor 430 may control the display 432 to display an instructional prompt instructing the user to correctly or properly orient the drug delivery device 302 relative to the patient's skin at block 917.

Next, the method 900 continues on to block 918, where the local computing device 304 receives, at the communication module 430, sensor data generated by the orientation sensors 364 and transmitted from the communication module 352 of the drug delivery device 302. Then, at block 920, the sensor data received at block 918 may be processed (e.g., analyzed) by the processor 420 of the local computing device 304 according to information stored in the memory 422 of the local computing device 304 to determine the orientation of the drug delivery device 304. The method 900 then continues to block 922 where the processor 430 compares the orientation determined at block 904 with information stored in the memory 422 to determine if the orientation of the drug delivery device relative to the patient's skin is acceptable. In response to a determination that the drug delivery device 302 is not correctly oriented relative to the patient's skin at block 922, the processor 430 may control the display 432 to display an instructional prompt instructing the user to reposition or reorient the drug delivery device 302 at block 924, and subsequently the method 900 may return to block 918. In response to a determination that the drug delivery device 302 is properly oriented relative to the patient's skin at block 922, the processor 430 may control the display 432 to display an instructional prompt instructing the user to actuate the drug delivery device 302 to deliver the medicament to the patient at block 926. In some embodiments, the drug delivery device 302 may be actuated by manually depressing the actuator 340.

The method 900 then continues on to block 928, where the local computing device 304 receives, at the communication module 430, sensor data generated by the switch 366 and transmitted from the communication module 352 of the drug delivery device 302. Then, at block 930, the sensor data received at block 928 may be processed (e.g., analyzed) by the processor 420 of the local computing device 304 according to information stored in the memory 422 of the local computing device 304 to determine if the drug delivery device 304 has been actuated. In response to a determination that the drug delivery device 302 has not been actuated at block 930, the method 900 may return to block 928. In response to a determination that the drug delivery device 302 has been actuated at block 930, the processor 430 may control the display 432 to display an instructional prompt instructing the user to wait for completion of a delivery of a medicament from the reservoir to the patient at block 932.

Next, the method 900 continues on to block 934, where the local computing device 304 receives, at the communication module 430, sensor data generated by the orientation sensors 364 and transmitted from the communication module 352 of the drug delivery device 302. Then, at block 936, the sensor data received at block 934 may be processed (e.g., analyzed) by the processor 420 of the local computing device 304 according to information stored in the memory 422 of the local computing device 304 to determine the orientation of the drug delivery device 304. The method 900 then continues to block 938 where the processor 430 compares the orientation determined at block 904 with information stored in the memory 422 to determine if the orientation of the drug delivery device relative to the patient's skin is acceptable. In response to a determination that the drug delivery device 302 is not correctly oriented relative to the patient's skin at block 938, the processor 430 may control the display 432 to display an instructional prompt instructing the user to reposition or reorient the drug delivery device 302 at block 940, and subsequently the method 900 may return to block 934. In response to a determination that the drug delivery device 302 is properly oriented relative to the patient's skin at block 938, the processor 430 may control the display 432 to display an instructional prompt instructing the user to wait for completion of a delivery of a medicament from the reservoir 312 to the patient at block 941.

The method 900 then continues to block 942, where the local computing device 304 receives, at the communication module 430, sensor data generated by a medicament fluid level sensor (not illustrated) associated with the reservoir 312 and transmitted from the communication module 352 of the drug delivery device 302. Then, at block 944, the sensor data received at block 942 may be processed (e.g., analyzed) by the processor 420 of the local computing device 304 according to information stored in the memory 422 of the local computing device 304 to determine if delivery of the medicament from the reservoir 312 to the patient has been completed. In some embodiments, the determination of the completion of medicament delivery may not be based on sensor data received from the drug delivery device 302, but instead on a timer monitored or maintained by the processor 420 and an estimate of the time required to eject the drug completely from the reservoir 312 according to previously performed time trials.

In response to a determination that the delivery of the medicament from the reservoir 312 to the patient is not complete at block 944, the processor 430 may control the display 432 to display an instructional prompt instructing the user to wait for completion of a delivery of a medicament from the reservoir 312 to the patient at block 946, and subsequently the method 900 may return to block 942. In response to a determination that the drug delivery device 302 is properly oriented relative to the patient's skin at block 944, the processor 430 may control the display 432 to display an instructional prompt instructing the user to discard the drug delivery device 302 at block 948.

Subsequently, the method 900 may proceed to block 950 where the processor 420 generates a report representative of completion of delivery of the medicament to the patient and controls the communication module 430 to transmit the report to another external computing device (e.g., the remote computing device 306) and/or to the drug delivery device 302.

The above description describes various sensors and sensor systems which can be used in combination with a drug delivery device for detecting a condition and/or operational state of the drug delivery device. Additional or alternative sensors and sensor systems can also be incorporated in the drug delivery devices described above, including any combination of the sensors and sensor systems disclosed in the co-filed International patent application entitled "Drug Delivery System and Method of Use" and having the entirety of which is hereby incorporated by reference.

The above description describes various systems and methods for use with a drug delivery device. It should be clear that the system, drug delivery device or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546;

A551; Ab553; Ab555; Ab558; Ab559; Ab565; AbF1AbFD; AbFE; AbFJ; AbFK; AbG1D4; AbGC1E8; AbH1C12; AblAl; AblF; AblK, AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath®

(alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP lIb/Ilia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-B. anthracis protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti- IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

It should be noted that the configurations of the various embodiments of the drug delivery devices and drug delivery systems described herein are illustrative only. Although only a few embodiments of the of the drug delivery devices and drug delivery systems have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, orientations, etc.) without materially departing from the novel teachings and advantages of the subject matter of this disclosure. For example, any combination of one or more of the sensors and/or controllable elements described herein may be incorporated into one or more of the drug delivery systems and drug delivery devices described herein. Also, the order or sequence of any process or method steps described herein may be varied or re-sequenced, in any combination, according to alternative embodiments. Furthermore, any combination of one or more of the elements of one or more of the claims set forth at the end of this disclosure is possible.

Although the preceding text sets forth a detailed description of different embodiments of the invention, it should be understood that the legal scope of the invention is defined by the words of the claims set forth at the end of this patent. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent, that would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed is:

1. A system comprising:
    a drug delivery device comprising:
        a reservoir;

a stopper movably disposed in the reservoir;

a delivery member having a proximal end in fluid communication with or configured to be in fluid communication with the reservoir and a distal end configured to be received within a patient;

one or more sensors comprising at least one sensor configured to monitor movement of the stopper in the reservoir;

a first communication module;

a first controller operably coupled with the one or more sensors and the first communication module, the first controller being configured to:

use the one or more sensors to determine at least one of a condition or an operational state of the drug delivery device, and control the first communication module to transmit a communication representative of at least one of the condition or the operational state of the drug delivery device; and an external computing device comprising:

a second communication module configured to receive the communication from the first communication module;

a display;

a memory; and a second controller operably coupled with the display to cause the display to display at least one of an instructional prompt or an informational prompt based on the communication from the first communication module, wherein the at least one of an instructional prompt or an informational prompt comprises an amount of a drug delivered to the patient determined at least partly based on information from the at least one sensor configured to monitor movement of the stopper in the reservoir.

2. The system of claim 1, wherein:

the first controller is configured to:

use the one or more sensors to determine a temperature or a temperature history of the drug delivery device, and control the first communication module to transmit a communication representative of the temperature or the temperature history of the drug delivery device; and the second controller is:

configured to compare the temperature or the temperature history of the drug delivery device to information stored in the memory of the external computing device to determine if the temperature or the temperature history of the drug delivery device is acceptable; and in response to a determination that the drug delivery device has an acceptable temperature or an acceptable temperature history, cause the display to display an instructional prompt instructing a user to dispose the drug delivery device on or against a skin of the patient.

3. The system of claim 1, wherein:

the first controller is configured to:

use the one or more sensors to determine if the drug delivery device contacts a skin of a patient, and control the first communication module to transmit a communication representative of contact between the drug delivery device and the skin of the patient; and in response to a determination that the drug delivery device contacts the skin of the patient, the second controller is operably coupled to the display to cause the display to display an instructional prompt instructing a user to correctly orient the drug delivery device relative to the skin of the patient.

4. The system of any one of claim 1, wherein:

the first controller is configured to:

use the one or more sensors to determine an orientation of the drug delivery device, and control the first communication module to transmit a communication representative of the orientation of the drug delivery device; and in response to a determination that the orientation of the drug delivery device is acceptable, the second controller is operably coupled to the display to cause the display to display an instructional prompt instructing a user to actuate the drug delivery device.

5. The system of any one of claim 1, wherein:

the first controller is configured to:

use the one or more sensors to determine if the user has actuated the drug delivery device, and control the first communication module to transmit a communication indicating that the drug delivery device has been actuated by the user; and in response to a determination that the drug delivery device has been actuated by a user, the second controller is operably coupled to the display to cause the display to display an instructional prompt instructing a user to wait for completion of a delivery of a medicament from the reservoir to the patient.

6. The system of any one of claim 1, wherein:

the first controller is configured to:

use the one or more sensors to determine if a delivery of a medicament from the reservoir to the patient has been completed, and control the first communication module to transmit a communication representative of completion of delivery of a medicament from the reservoir to the patient; and in response to a determination that the delivery of the medicament from the reservoir to the patient has been completed, the second controller operably coupled to the display to cause the display to display an instructional prompt instructing a user to discard the drug delivery device.

7. The system of claim 1, the one or more sensors comprising a temperature sensor configured to detect a temperature of a medicament within the reservoir.

8. The system of claim 1, the one or more sensors comprising at least one of:

a skin contact sensor including at least one of a pressure sensor, a capacitance sensor, a resistance sensor, or an inductance sensor, or an orientation sensor.

9. The system of claim 1, the external computing device comprising at least one of a smartphone, a smartwatch, a smart wearable device, a personal computer, a laptop computer, a smart television, a smart appliance, a smart automobile, a networked computer, or a tablet computer.

10. The system of claim 1, the first communication module being configured to communicate with the second communication module via at least one of Bluetooth, Bluetooth low energy, radio-frequency identification (RFID), Zigbee, Wi-Fi, or near field communication (NFC).

11. The system of claim 1, wherein the reservoir comprises a medicament, the medicament being selected from the group consisting of: TNF inhibitors, antibodies to the calcitonin gene-related peptide receptor, granulocyte colony stimulating factors, erythropoiesis stimulating agents, apelin receptor agonists, antibodies to proprotein convertase subtilisin/kexin Type 9 (PCSK9), and tissue inhibitors of metalloproteinases.

12. A method of using a system comprising a drug delivery device and an external computing system, the drug delivery device comprising a reservoir, a stopper movably disposed in the reservoir, at least one sensor configured to monitor movement of the stopper in the reservoir, and a delivery member having a proximal end in fluid communication or configured to be in fluid communication with the reservoir and a distal end configured to be received within a patient, the external computing device comprising a memory, the method comprising:

determining at least one of a condition or an operational state of the drug delivery device;

transmitting a communication representative of at least one of the condition or the operational state from the drug delivery device;

receiving the communication from the drug delivery device at the external computing device;

processing the communication received from the drug delivery device according to information stored in the memory of the external computing device; and displaying, by the external computing device, at least one of an instructional prompt or an informational prompt based on the communication received from the drug delivery device, wherein the at least one of an instructional prompt or an informational prompt comprises an amount of a drug delivered to the patient determined at least partly based on information from the at least one sensor configured to monitor movement of the stopper in the reservoir.

13. The method of claim 12, comprising displaying the at least one of an instructional prompt or an informational prompt according to: (i) the communication received from the drug delivery device, and (ii) the information stored in the memory of the external computing device.

14. The method of claim 12, wherein the determining of the at least one of the condition or the operational state of the drug delivery device comprises determining, with the drug delivery device, a temperature or a temperature history of the drug delivery device based on the sensor data.

15. The method of claim 14, comprising:

comparing the temperature or the temperature history of the drug delivery device to the information stored in the memory of the external computing device to determine if the temperature or the temperature history of the drug delivery device is acceptable; and in response to a determination that the drug delivery device has an acceptable temperature or an acceptable temperature history, displaying an instructional prompt instructing a user to dispose the drug delivery device on or against a skin of the patient.

16. The method of claim 12, the determining of the at least one of the condition or the operational state of the drug delivery device comprising determining, with the drug delivery device, if the drug delivery device is disposed on or against a skin of a patient based on the sensor data.

17. The method of claim 16, comprising, in response to a determination that the drug delivery device is disposed on or against the skin of the patient, displaying an instructional prompt instructing a user to correctly orient the drug delivery device relative to the skin of the patient.

18. The method of claim 17, the determining of the at least one of the condition or the operational state of the drug delivery device comprising determining, with the drug delivery device, an orientation of the drug delivery device based on the sensor data.

19. The method of claim 18, comprising:

comparing the orientation of the drug delivery device to the information stored in the memory of the external computing device to determine if the orientation of the drug delivery device relative to a skin of a patient is acceptable; and in response to a determination that the orientation of the drug delivery device is acceptable, displaying an instructional prompt instructing a user to actuate the drug delivery device.

20. The method of claim 17, the determining of the at least one of the condition or the operational state of the drug delivery device comprising determining, with the drug delivery device, if the drug delivery device has been actuated by a user based on the sensor data.

21. The method of claim 20, comprising, in response to a determination that the drug delivery device has been actuated by the user, displaying an instructional prompt instructing a user to wait for completion of a delivery of a medicament from the reservoir to the patient.

22. The method of claim 17, the determining of the at least one of the condition or the operational state of the drug delivery device comprising determining, with the drug delivery device, if a delivery of a medicament from the reservoir to a patient has been completed based on the sensor data.

23. The method of claim 22, comprising, in response to a determination that the delivery of the medicament from the reservoir to the patient has been completed, displaying an instructional prompt instructing a user to discard the drug delivery device.

24. The method of claim 17, wherein the communication is transmitted via at least one of Bluetooth, Bluetooth low energy, radio-frequency identification (RFID), Zigbee, Wi-Fi, or near field communication (NFC).

25. The method of claim 17, wherein the reservoir comprises a medicament, the medicament being selected from the group consisting of: TNF inhibitors, antibodies to the calcitonin gene-related peptide receptor, granulocyte colony stimulating factors, erythropoiesis stimulating agents, apelin receptor agonists, antibodies to proprotein convertase subtilisin/kexin Type 9 (PCSK9), and tissue inhibitors of metalloproteinases.

26. A method of monitoring use of a drug delivery device with an application executing on a mobile computing device including a processor and a memory, the method comprising:

collecting, with or via at least one sensor coupled with the drug delivery device, sensor data related to use of the drug delivery device to deliver a drug to a patient;

transmitting, from the drug delivery device to the mobile computing device, a report comprising a unique identifier for the drug delivery device and drug delivery information based on the sensor data collected with or via the at least one sensor coupled with the drug delivery device when the drug delivery device delivers the drug to the patient; and further comprising:

displaying the report on a display of the mobile computing device, and/or configuring the report, with the processor of the mobile computing device, to be transmitted by the mobile computing device to a remote computing device.

27. The method of claim 26, wherein the drug delivery information comprises at least one of: a status of delivery trigger, a status of device application to the patient, a status of cannula insertion, a status of drug delivery, and a status of delivery completion.

* * * * *